US009988380B2

(12) United States Patent
Givskov et al.

(10) Patent No.: US 9,988,380 B2
(45) Date of Patent: Jun. 5, 2018

(54) QUORUM SENSING INHIBITORS

(71) Applicants: Nanyang Technological University, Singapore (SG); National University of Singapore, Singapore (SG)

(72) Inventors: Michael Givskov, Singapore (SG); Liang Yang, Singapore (SG); Yang Yi Sean Tan, Singapore (SG)

(73) Assignees: Nanyang Technological University, Singapore (SG); National University of Singapore, Singapore (SG)

(*) Notice: Subject to any disclaimer, the term of this patent is extended or adjusted under 35 U.S.C. 154(b) by 0 days. days.

(21) Appl. No.: 14/762,770

(22) PCT Filed: Mar. 10, 2014

(86) PCT No.: PCT/SG2014/000115
§ 371 (c)(1),
(2) Date: Jul. 22, 2015

(87) PCT Pub. No.: WO2014/142748
PCT Pub. Date: Sep. 18, 2014

(65) Prior Publication Data
US 2015/0353545 A1 Dec. 10, 2015

Related U.S. Application Data

(60) Provisional application No. 61/782,477, filed on Mar. 14, 2013.

(51) Int. Cl.
| | |
|---|---|
| C07D 487/04 | (2006.01) |
| A61K 31/519 | (2006.01) |
| A61P 31/04 | (2006.01) |
| C07D 471/04 | (2006.01) |
| C07D 209/42 | (2006.01) |
| C07C 229/36 | (2006.01) |
| A01N 37/44 | (2006.01) |
| A01N 43/38 | (2006.01) |
| A01N 43/90 | (2006.01) |

(52) U.S. Cl.
CPC .......... *C07D 471/04* (2013.01); *A01N 37/44* (2013.01); *A01N 43/38* (2013.01); *A01N 43/90* (2013.01); *A61K 31/519* (2013.01); *C07C 229/36* (2013.01); *C07D 209/42* (2013.01); *C07D 487/04* (2013.01)

(58) Field of Classification Search
CPC ............................ C07D 487/04; A61K 31/519
USPC ....................................... 544/254; 514/261.1
See application file for complete search history.

(56) References Cited

PUBLICATIONS

Singh S.B., Bioorganic & Medicinal Chemistry Letters 24 (2014) 3683-3689.*
Wilson D.N.,Critical Reviews in Biochemistry and Molecular Biology, 2009;44(6): 393-433.*
Maguire B.A., Microbiology and Molecular Biology Reviews, Mar. 2009, p. 22-35.*
Rehm et al.,Clinical Infectious Diseases 2010; 51 (2):176-182.*
Freshney et al.,Culture of Animal Cells, A Manual of Basic Technique, Alan R. Liss, Inc., 1983, New York, p. 4.*
Dermer et al., Bio/Technology, 1994, 12:320.*
Bassetti et al. Annals of Clinical Microbiology and Antimicrobials 2013, 12:22, pp. 1-15.*
Shaffer Yale Journal of Biology and MEDiCiNE 86 (2013), pp. 261-270.*
Theuretzbacher et al. Current Opinion in Pharmacology, 2011, 11 : 429-432.*
Kint et al. Trends in Microbiology, Dec. 2012, vol. 20, No. 12, 577-585.*
Becker D.E. Anesth Prog 60:111-123, 2013.*
Babic et al., Drug Resistance Updates 9, 142-156, 2006.*
Paterson et al., Clinical Microbiological reviews 18(40, 657-686, 2005.*
Allesen-Holm et al., "A characterization of DNA release in *Pseudomonas aeruginosa* cultures and biofilms," *Molecular Microbiology* 59(4):1114-1128, 2006.
Andersen et al., "New Unstable Variants of Green Fluorescent Protein for Studies of Transient Gene Expression in Bacteria," *Applied and Environmental Microbiology* 64(6):2240-2246, Jun. 1998.
Annapoorani et al., "Computational discovery of putative quorum sensing inhibitors against LasR and RhlR receptor proteins of *Pseudomonas aeruginosa,*" *J. Comput. Aided Mol. Des.* 26:1067-1077, 2012.
Bassler et al., "Bacterially Speaking," *Cell* 125, 237-246, Apr. 21, 2006.
Bottomley et al., "Molecular Insights into Quorum Sensing in the Human Pathogen *Pseudomonas aeruginosa* from the Structure of the Virulence Regulator LasR Bound to Its Autoinducer," *The Journal of Biological Chemistry* 282(18):13592-13600, May 4, 2007.
Brackman et al., "Use of quorum sensing inhibitors to interfere with biofilm formation and development in *Burkholderia multivorans* and *Burkholderia cenocepacia,*" *Research in Microbiology* 160:144-151, 2009.
Cornelis et al., "A new regulator linking quorum sensing and iron uptake in *Pseudomonas aeruginosa,*" Microbiology 150:752-756, Apr. 2004.
Cunliffe et al., "Cloning and Characterization of *pvdS*, a Gene Required for Pyoverdine Synthesis in *Pseudomonas aeruginosa*: PvdS Is Probably an Alternative Sigma Factor," *Journal of Bacteriology* 177(10):2744-2750, May 1995.
Dunkel et al., "SuperNatural: a searchable database of available natural compounds," *Nucleic Acids Research* 34:D678-D683, 2006.
Engel et al., "Protease IV, a Unique Extracellular Protease and Virulence Factor from *Pseudomonas aeruginosa,*" *The Journal of Biological Chemistry* 273(27):16792-16797, 1998.
Finnan et al., "Genome Diversity of *Pseudomonas aemginosa* Isolates from Cystic Fibrosis Patients and the Hospital Environment," *Journal of Clinical Microbiology* 42(12):5783-5792, Dec. 2004.

(Continued)

*Primary Examiner* — Venkataraman Balasubramanian
(74) *Attorney, Agent, or Firm* — Seed IP Law Group LLP

(57) ABSTRACT

The invention relates to compounds for use as quorum sensing inhibitors, and in particular, to quorum sensing inhibitors of *Pseudomonas aeruginosa*.

2 Claims, 21 Drawing Sheets

(56) References Cited

PUBLICATIONS

Fletcher et al., "Biosensor-based assays for PQS, HHQ and related 2-alkyl-4-quinolone quorum sensing signal molecules," *Nature Protocols* 2(5):1254-1262, 2007.

Friesner et al., "Glide: A New Approach for Rapid, Accurate Docking and Scoring. 1. Method and Assessment of Docking Accuracy," *J. Med. Chem.* 47:1739-1749, 2004.

Fuqua et al., "Quorum Sensing in Bacteria: the LuxR-LuxI Family of Cell Density-Responsive Transcriptional Regulators," *Journal of Bacteriology* 176(2):269-275, Jan. 1994.

Fuqua et al., "Regulation of Gene Expression by Cell-to-Cell Communication: Acyl-Homoserine Lactone Quorum Sensing," *Annu. Rev. Genet.* 35 :439-468, 2001.

Gambello et al., "Cloning and Characterization of the *Pseudomonas aeruginosa* lasR Gene, a Transcriptional Activator of Elastase Expression," *Journal of Bacteriology* 173(9):3000-3009, May 1991.

Gambello et al., "LasR of *Pseudomonas aeruginosa* Is a Transcriptional Activator of the Alkaline Protease Gene (*apr*) and an Enhancer of Exotoxin A Expression," *Infection and Immunity* 61(4):1180-1184, Apr. 1993.

Geske et al., "Modulation of Bacterial Quorum Sensing with Synthetic Ligands: Systematic Evaluation of N-Acylated Homoserine Lactones in Multiple Species and New Insights into Their Mechanism of Action," *J. Am. Chem. Soc.* 129:13613-13625, 2007.

Ghosh et al., "Structure-based virtual screening of chemical libraries for drug discovery," *Current Opinion in Chemical Biology* 10:194-202, 2006.

Goede et al., "SuperDrug: a conformational drug database," *Bioinformatics* 21(9):1751-1753, 2005.

Hentzer et al., "Attenuation of *Pseudomonas aeruginosa* virulence by quorum sensing inhibitors," *The EMBO Journal* 22(15):3803-3815, 2003.

Hentzer et al., "Inhibition of quorum sensing in *Pseudomonas aeruginosa* biofilm bacteria by a halogenated furanone compound," *Microbiology* 148:87-102, 2002.

Hentzer et al., "Pharmacological inhibition of quorum sensing for the treatment of chronic bacterial infections," *The Journal of Clinical Investigation* 112(9):1300-1307, Nov. 2003.

Jain, "Surflex: Fully Automatic Flexible Molecular Docking Using a Molecular Similarity-Based Search Engine," *J. Med. Chem.* 46:499-511, 2003.

Jensen et al., "RhlR Expression in *Pseudomonas aeruginosa* Is Modulated by the *Pseudomonas* Quinolone Signal via PhoB-Dependent and—Independent Pathways," *Journal of Bacteriology* 188(24):8601-8606, Dec. 2006.

Kaldor et al., "Viracept (Nelfinavir Mesylate, AG1343): A Potent, Orally Bioavailable Inhibitor of HIV-1 Protease," *J.Med. Chem.* 40:3979-3985, 1997.

Kalia et al., "Nucleotide, c-di-GMP, c-di-AMP, cGMP, cAMP, (p)ppGpp signaling in bacteria and implications in pathogenesis," *Chem. Soc. Rev.* 42:305-341, 2013.

Kiran et al., "Discovery of a Quorum-Sensing Inhibitor of Drug-Resistant Staphylococcal Infections by Structure-Based Virtual Screening," *Molecular Pharmacology* 73(5):1578-1586, 2008.

Lagorce et al., "DG-AMMOS: A New tool to generate 3D conformation of small molecules using Distance Geometry and Automated Molecular Mechanics Optimization for in silico Screening," *BMC Chemical Biology* 9(6), 2009, 10 pages.

Lamont et al., "Siderophore-mediated signaling regulates virulence factor production in *Pseudomonas aeruginosa*," *Proc. Natl. Acad. Sci. USA* 99(10):7072-7077, May 14, 2002.

Leoni et al., "Iron-Regulated Transcription of the *pvdA* Gene in *Pseudomonas aeruginosa*: Effect of Fur and PvdS on Promoter Activity," *Journal of Bacteriology* 178(8):2299-2313, Apr. 1996.

Li et al., "Structure-Based Discovery and Experimental Verification of Novel AI-2 Quorum Sensing Inhibitors against *Vibrio harveyi*," *ChemMedChem* 3:1242-1249, 2008.

Liu et al., "Synergistic Activities of an Efflux Pump Inhibitor and Iron Chelators against *Pseudomonas aeruginosa* Growth and Biofilm Formation," *Antimicrobial Agents and Chemotherapy* 54(9):3960-3963, Sep. 2010.

McGrath et al., "Dueling quorum sensing systems in *Pseudomonas aeruginosa* control the production of the *Pseudomonas* quinolone signal (PQS)," *FEMS Microbiology Letters* 230:27-34, 2004.

Miller et al., "Quorum Sensing in Bacteria," *Annu. Rev. Microbiol.* 55:165-199, 2001.

Müh et al., "Novel *Pseudomonas aeruginosa* Quorum-Sensing Inhibitors Identified in an Ultra-High-Throughput Screen," *Antimicrobial Agents and Chemotherapy* 50(11):3674-3679, Nov. 2006.

Nouwens et al., "Proteome analysis of extracellular proteins regulated by the *las* and *rhl* quorum sensing systems in *Pseudomonas aeruginosa* PAO1," *Microbiology* 149:1311-1322, 2003.

Obritsch et al., "Nosocomial Infections Due to Multidrug-Resistant *Pseudomonas aeruginosa*: Epidemiology and Treatment Options," *Pharmacology* 25(10):1353-1364, 2005.

Ochsner et al., "Autoinducer-mediated regulation of rhamnolipid biosurfactant synthesis in *Pseudomonas aeruginosa*," *Proc. Natl. Acad. Sci USA* 92:6424-6428, Jul. 1995.

Passador et al., "Expression of Pseudomonas aeruginosa Virulence Genes Requires Cell-to-Cell Communication," *Science* 260(5111):1127-1130, May 21, 1993.

Pearson et al., "Roles of *Pseudomonas aeruginosa las* and *rhl* Quorum-Sensing Systems in Control of Elastase and Rhamnolipid Biosynthesis Genes," *Journal of Bacteriology* 179(18):5756-5767, Sep. 1997.

Pearson et al., "Structure of the autoinducer required for expression of *Pseudomonas aeruginosa* virulence genes," *Proc. Natl. Acad. Sci. USA* 91:197-201, Jan. 1994.

Pesci et al., "Quinolone Signaling in the Cell-to-Cell Communication System of Pseudomonas aeruginosa," *Proc. Natl. Acad. Sci. USA* 96:11229-11234, Sep. 28, 1999.

Pesci et al., "Regulation of *las* and *rhl* Quorum Sensing in *Pseudomonas aeruginosa*," *Journal of Bacteriology* 179(10):3127-3132, May 1997.

Rasmussen et al., "Identity and effects of quorum-sensing inhibitors produced by *Penicillium* species," *Microbiology* 151:1325-1340, 2005.

Rasmussen et al., "Quorum-sensing inhibitors as anti-pathogenic drugs," *International Journal of Medical Microbiology* 296:149-161, 2006.

Rasmussen et al., "Screening for Quorum-Sensing Inhibitors (QSI) by Use of a Novel Genetic System, the QSI Selector," *Journal of Bacteriology* 187(5):1799-1814, Mar. 2005.

Ravichandiran et al., "Structure-based virtual screening for plant-derived SdiA-selective ligands as potential antivirulent agents against uropathogenic *Escherichia coli*," *European Journal of Medicinal Chemistry* 48:200-205, 2012.

SciFinder, CAS Registry No. 134-58-7, 5 pages.
SciFinder, CAS Registry No. 2683-90-1, 5 pages.
SciFinder, CAS Registry No. 456-88-2, 5 pages.
SciFinder, CAS Registry No. 69-96-5, 4 pages.
SciFinder, CAS Registry No. 771-50-6, 6 pages.

Shoichet, "Virtual screening of chemical libraries," *Nature*, 432:862-866, Dec. 16, 2004.

Skovstrup et al., "Identification of LasR Ligands through a Virtual Screening Approach," *ChemMedChem* 8:157-163, 2013.

Smith et al., "Library Screening for Synthetic Agonists and Antagonists of a *Pseudomonas aeruginosa* Autoinducer," *Chemistry & Biology* 10:563-571, Jun. 2003.

Stintzi et al., "Quorum-sensing and siderophore biosynthesis in *Pseudomonas aeruginosa: lasR/lasI* mutants exhibit reduced pyoverdine biosynthesis," *FEMS Microbiology Letters* 166:341-345, 1998.

Taguchi et al., "The Siderophore Pyoverdine of *Pseudomonas syringae* pv. tabaci 6605 Is an Intrinsic Virulence Factor in Host Tobacco Infection," *Journal of Bacteriology* 192(1):117-126, 2010.

Tan et al., "Identification of Five Structurally Unrelated Quorum-Sensing Inhibitors of *Pseudomonas aeruginosa* from a Natural-Derivative Database," *Antimicrobial Agents and Chemotherapy* 57(11):5629-5641, Nov. 2013.

(56) References Cited

OTHER PUBLICATIONS

Thomsen et al., "MolDock: A New Technique for High-Accuracy Molecular Docking," *J. Med. Chem.* 49:3315-3321, 2006.

Vannini et al., "The crystal structure of the quorum sensing protein TraR bound to its autoinducer and target DNA," *The EMBO Journal* 21(17):4393-4401, 2002.

von Itzstein et al., "Rational design of potent sialidase-based inhibitors of influenza virus replication," *Nature* 363:418-423, Jun. 3, 1993.

Wagner et al., "Microarray Analysis of *Pseudomonas aeruginosa* Quorum-Sensing Regulons: Effects of Growth Phase and Environment," *Journal of Bacteriology* 185(7):2080-2095, Apr. 2003.

Whitchurch et al., "Extracellular DNA Required for Bacterial Biofilm Formation," *Science* 295:1487, Feb. 22, 2002.

Whiteley et al., "Identification of genes controlled by quorum sensing in *Pseudomonas aeruginosa*," *Proc. Natl. Acad. Sci. USA* 96(24):13904-13909, Nov. 23, 1999.

Wilderman et al., "Characterization of an Endoprotease (PrpL) Encoded by a PvdS-Regulated Gene in *Pseudomonas aeruginosa*," *Infection and Immunity* 69(9):5385-8394, Sep. 2001.

Yang et al., "Computer-Aided Identification of Recognized Drugs as *Pseudomonas aeruginosa* Quorum-Sensing Inhibitors," *Antimicrobial Agents and Chemotherapy* 53(6):2432-2443, Jun. 2009.

Yang et al., "Effects of iron on DNA release and biofilm development by *Pseudomonas aeruginosa*," *Microbiology* 153:1318-1328, 2007.

Zou et al., "Molecular Basis for the Recognition of Structurally Distinct Autoinducer Mimics by the *Pseudomonas aeruginosa* LasR Quorum-Sensing Signaling Receptor," *Chemistry & Biology* 16:961-970, Sep. 25, 2009.

\* cited by examiner

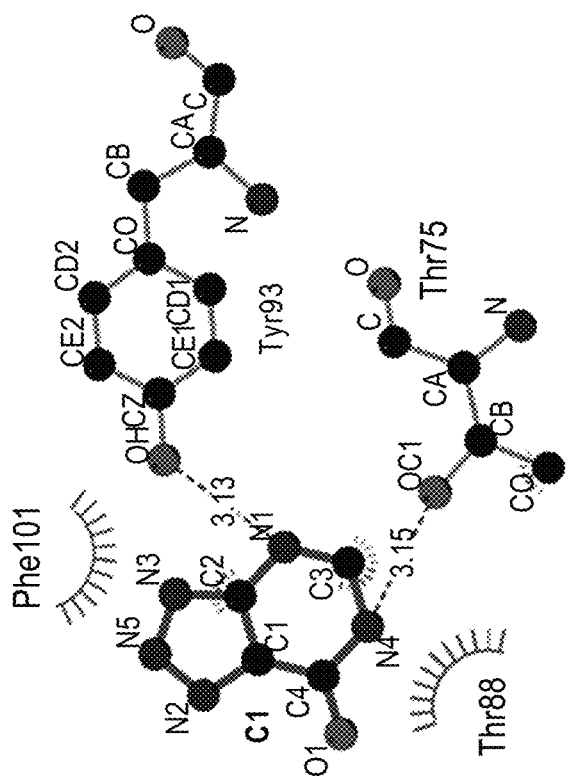
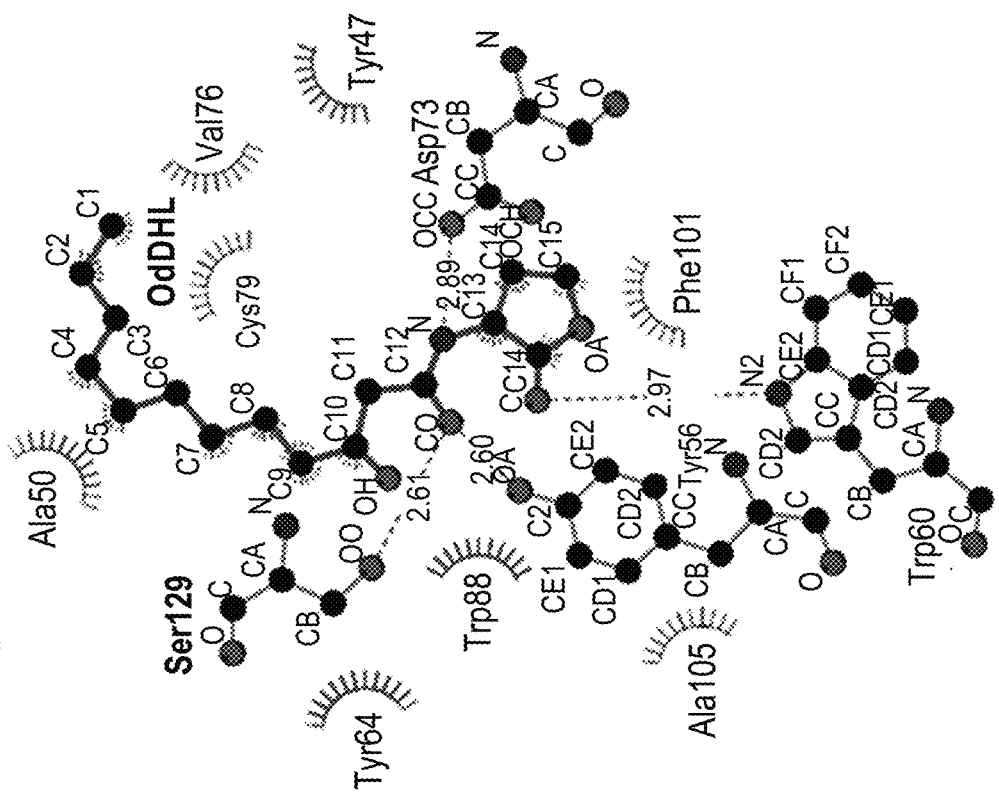
FIG. 4B
FIG. 4A

Table 1. List of *P. aeruginosa* and *E. coli* strains used in the present study.

| Species | Name/Genotype | Description[a] |
|---|---|---|
| *P. aeruginosa* | PAO1 | Wild-type |
| | PAO1-gfp | Gfp-tagged wild-type |
| | PAO1/*lasB-gfp* | Gm[r]; PAO1 containing *lasB-gfp*(ASV) reporter fusion |
| | PAO1/*rhlA-gfp* | Gm[r]; PAO1-ATCC, *rhlA-gfp*(ASV) reporter fusion |
| | PAO1/*pqsA-gfp* | Gm[r]; PAO1-ATCC, *pqsA-gfp*(ASV) reporter fusion |
| | PAO1 Δ*lasR* | PAO1 *lasR* mutant |
| | PAO1 Δ*lasR/rhlA-gfp* | Gm[r]/Carb[r]; PAO1 *lasR* mutant, *rhlA-gfp*(ASV) reporter fusion |
| | PAO1 Δ*lasR/pqsA-gfp* | Gm[r]/Carb[r]; PAO1 *lasR* mutant, *rhlA-gfp*(ASV) reporter fusion |
| *E. coli* | MT102 | Wild-type |
| | MT102/*lasB-gfp* | MT102 containing *lasB-gfp*(ASV) reporter fusion |

[a]Description of the strains' antibiotic resistance. Gm[r]: gentamycin resistance. Carb[r]: carbenicillin resistance.

FIG. 11

| Compound | Residues within the LasR Ligand Binding Pocket Having H-bonding interactions with Ligand |
|---|---|
| OdDHL | Tyr 56, Trp 60, Asp 73, Ser 129 |
| C1 | Thr 75, Tyr 93 |
| F1 | Thr 75, Tyr 93 |
| G1 | Trp 60, Thr 75, Tyr 93 |
| H1 | Tyr 56, Thr 75, Ser 129 |
| F2 | Tyr 56, Ser 129 |

FIG. 12

| PA No. | Gene name | Description of Product[a] | Peptides (95%) | Coverage (95%) | 115:114[b] | p-value 115:114 |
|---|---|---|---|---|---|---|
| PA3862 | dauB | NAD(P)H-dependent anabolic L-arginine dehydrogenase, DauB | 12 | 58.41 | 0.23 | 2.91E-03 |
| PA4175 | piv/prpL | protease IV | 16 | 35.93 | 0.29 | 9.87E-03 |
| PA5100 | hutU | urocanatehydratase [Pseudomonas aeruginosa MPAO1/P2] | 13 | 34.88 | 0.39 | 3.80E-04 |
| PA3922 | - | conserved hypothetical protein | 10 | 29.23 | 0.42 | 4.90E-03 |
| PA3919 | - | conserved hypothetical protein | 18 | 41.47 | 0.43 | 8.84E-03 |
| PA2300 | chiC | chitinase | 16 | 36.85 | 0.44 | 3.65E-05 |
| PA1372 | - | hypothetical protein PA1372 | 12 | 24.47 | 0.45 | 4.52E-03 |
| PA0572 | - | hypothetical protein PA0572 | 12 | 20.26 | 0.46 | 8.03E-03 |
| PA0792 | prpD | propionate catabolic protein PrpD | 31 | 51.21 | 0.47 | 2.98E-04 |
| PA0400 | metBmetC | probable cystathionine gamma-lyase | 76 | 62.94 | 0.49 | 2.97E-02 |
| PA5213 | gcvP1 | glycine cleavage system protein P1 | 9 | 15.66 | 0.52 | 2.54E-02 |
| PA2951 | etfA | electron transfer flavoprotein alpha-subunit | 87 | 65.37 | 0.52 | 3.87E-02 |
| PA0586 | - | conserved hypothetical protein | 9 | 20.89 | 0.53 | 3.21E-02 |
| PA2399 | pvdD | pyoverdinesynthetase D | 126 | 45.55 | 0.54 | 2.49E-05 |
| PA3924 | - | probable medium-chain acyl-CoA ligase | 10 | 32.32 | 0.54 | 1.24E-02 |
| PA2290 | gcd | glucose dehydrogenase | 24 | 35.74 | 0.59 | 4.22E-03 |
| PA2424 | pvdL | pyoverdinechromophoresynthetasePvdL | 368 | 50.25 | 0.60 | 0.00E+00 |
| PA3148 | wbpI | UDP-N-acetylglucosamine 2-epimerase WbpI | 53 | 65.54 | 0.60 | 5.85E-03 |
| PA2302 | ambE | AmbE. Involved in L-2-amino-4-methoxy-trans-3-butenoic acid (AMB) biosynthesis | 49 | 31.45 | 0.61 | 4.46E-07 |
| PA2402 | - | probable non-ribosomal peptide synthetase | 273 | 41.58 | 0.62 | 2.46E-10 |
| PA0852 | - | chitin-binding protein CbpD precursor | 16 | 36.76 | 0.62 | 1.41E-02 |
| PA3083 | pepN | aminopeptidase N | 50 | 36.27 | 0.63 | 1.72E-02 |
| - | - | putative ClpA/B protease ATP binding subunit [Pseudomonas aeruginosa MPAO1/P2] | 30 | 36.05 | 0.63 | 2.90E-03 |
| PA0588 | - | conserved hypothetical protein | 49 | 41.25 | 0.64 | 4.74E-04 |
| PA2445 | gcvP2 | glycine cleavage system protein P2 | 143 | 51.51 | 0.64 | 9.94E-04 |
| PA0399 | - | cystathionine beta-synthase | 64 | 68.71 | 0.64 | 4.28E-03 |
| PA5172 | - | ornithine carbamoyltransferase, catabolic | 47 | 44.94 | 0.65 | 7.22E-03 |

[a] Description is obtained from the *Pseudomonas* Genome Database (Winsor et al., 2011) (http://www.pseudomonas.org)
[b] 115:114 refers to the ratio of the protein's abundance in the G1-treated sample (115) compared to the untreated control (114).

FIG. 13

| IUPAC Name | Structure | Molecular Weight | Rerank Score | Ligand Efficiency |
|---|---|---|---|---|
| 3-Oxo-C12-HSL (OdDHL) | 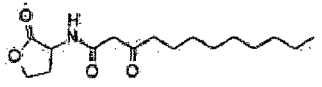 | 297.39 | -81.2886 | -3.87089 |
| Patulin | 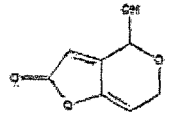 | 154.12 | -62.0131 | -5.63755 |
| Salicylic acid | 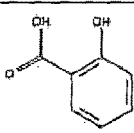 | 137.113 | -63.5007 | -6.35007 |
| 3-Oxo-C12-(2-aminophenol) | 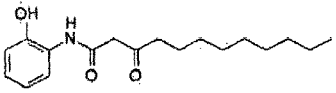 | 305.412 | -77.6409 | -3.52913 |
| Furanone C30 | 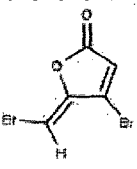 | 252.868 | -62.0532 | -6.89479 |
| 4-Nitropyridine-*N*-oxide | 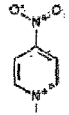 | 140.097 | -63.2568 | -6.32568 |
| Nifuroxazide | 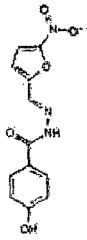 | 275.217 | -20.4001 | -1.02001 |
| Chlorzoxazone | 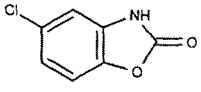 | 168.557 | -72.5769 | -6.5979 |
FIG. 14

| ID | IUPAC Name | Structure | Molecular Weight | Rerank Score | Ligand Efficiency |
|---|---|---|---|---|---|
| A1 | 7-aminodecanoic acid | 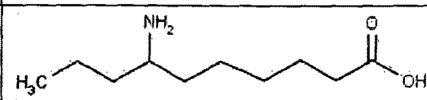 | 186.271 | -64.26 | -4.94 |
| B1 | 2-prop-2-enyloxy-2H-3,4,5,6-tetrahydropyran | 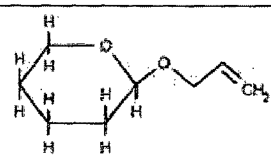 | 137.156 | -62.71 | -6.27 |
| C1 | 6-hydro-3H-1,2,3-triazolo[5,4-d]pyrimidin-7-one | 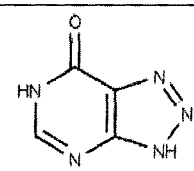 | 136.092 | -64.15 | -6.41 |
| D1 | methyl 3-(3,5-dioxo-2H,4H-1,2,4-triazin-6-yl)propanoate | 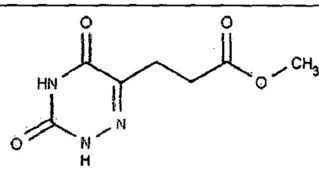 | 199.164 | -69.15 | -4.94 |
| E1 | xanthen-9-one | 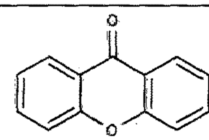 | 196.201 | -74.45 | -4.96 |
| F1 | 2-amino-3-(3-fluorophenyl)propanoic acid | 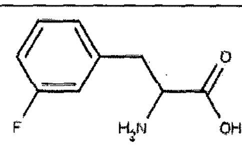 | 182.172 | -70.69 | -5.44 |
| G1 | 5-imino-4,6-dihydro-3H-1,2,3-triazolo[5,4-d]pyrimidin-7-one | 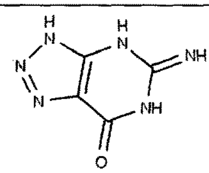 | 151.106 | -69.93 | -6.36 |
| H1 | 2-amino-3-hydroxy-3-phenylpropanoic acid | 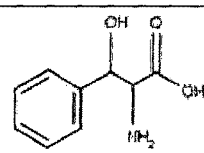 | 180.181 | -67.92 | -5.22 |
| A2 | (2R,6R)-2,6-diaminoheptanedioic acid | 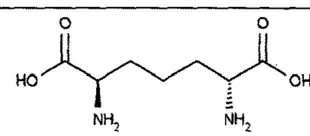 | 188.181 | -68.80 | -5.29 |

FIG. 15

| | | | | | |
|---|---|---|---|---|---|
| B2 | 4-[1-hydroxy-2-(methylamino)ethyl]benzene-1,2-diol, chloride | | 183.204 | -60.05 | -4.62 |
| C2 | 3-acetyl-2-oxo-3-hydrobenzoxazole | | 177.157 | -61.49 | -4.73 |
| D2 | 2-(5-hydroxyindol-3-yl)acetic acid | | 185.136 | -65.42 | -4.67 |
| E2 | methyl (2S,4R)-4-hydroxypyrrolidine-2-carboxylate, chloride | | 145.156 | -71.23 | -7.12 |
| F2 | indole-3-carboxylic acid | | 159.141 | -69.33 | -5.78 |
| G2 | 5-hydroxybenzo[d]1,3-oxathiolan-2-one | | 168.17 | -71.13 | -6.47 |
| H2 | 3,4-dihydroisoquinoline-6,7-diol | | 163.173 | -72.14 | -6.01 |
| A3 | methyl 3,5-dihydroxybenzoate | | 162.099 | -67.71 | -5.64 |
| B3 | 6-methoxy-3,4-dihydroisoquinolin-7-ol | | 177.2 | -74.23 | -5.71 |

FIG. 15 (continued)

| | | | | | |
|---|---|---|---|---|---|
| C3 | 6,7-dihydroimidazo[5,4-c]pyridine-6-carboxylic acid | | 163.133 | -75.50 | -6.29 |
| D3 | 5-methyl-1-(2-methylpropyl)-1,3-dihydropyrimidine-2,4-dione | | 182.22 | -60.08 | -4.62 |
| E3 | 2-(purin-6-ylamino)acetic acid | | 190.139 | -77.05 | -5.51 |
| F3 | methyl 2-oxopyran-3-carboxylate | | 154.12 | -68.61 | -6.24 |

FIG. 15 (continued)

| Import Molecules | |
|---|---|
| Preparation | |
|     Assign bonds | If missing |
|     Assign bond orders and hybridization | If missing |
|     Create explicit hydrogens | If missing |
|     Assign charges (calculated by MVD) | Always |
|     Detect flexible torsions in ligands | Always |
|     Assign Tripos atom types | If missing |
| Template docking wizard | |
|     Similarity measure | (Radius, strength, count) |
|     Steric | 1.8, 0.5, 21 |
|     Hydrogen donor | 1.8, 1, 3 |
|     Hydrogen acceptor | 1.8, 1, 4 |
|     Ring | 1.8, 1, 5 |
| Docking wizard | |
| Template docking: Docking using Ligand Template | |
|     Scoring strength | -500.00 |
|     Energy grid resolution (Å) | 0.20 |
| Scoring function | |
|     Score | Ligand evaluator |
|     Steric interactions | Yes |
|     Torsional interactions | Yes |
| Binding site | |
|     Center (x,y,z) | 24.07, 18.19, 77.44 |
|     Radius | 9 |
| Search algorithm | |
|     Algorithm | MolDock Optimizer |
|     Number of runs | 10 |
| Parameter settings | |
|     Constrain poses to cavity | Yes |
|     Population size | 50 |
|     Max Iterations | 2000 |
|     Scaling factor | 0.50 |
|     Crossover rate | 0.90 |
|     Offspring scheme | Scheme 1 |
|     Termination scheme | Variance-based |
| Pose clustering | |
|     Multiple poses | Return one pose for each run |
|     Tabu clustering | Yes |
|     RMSD threshold | 2.00 |
|     RMSD calculation | By atom ID (fast) |
|     Energy penalty | 100.00 |

FIG. 16

QUORUM SENSING INHIBITORS

CROSS-REFERENCE TO RELATED APPLICATION

This application claims the benefit of priority of U.S. Provisional Patent Application No. 61/782,477, filed Mar. 14, 2013, the contents of which being hereby incorporated by reference in its entirety for all purposes.

TECHNICAL FIELD

The invention relates to compounds for use as quorum sensing inhibitors (QSIs), and in particular, to quorum sensing inhibitors of Pseudomonas aeruginosa.

BACKGROUND

Bacteria communicate via a phenomenon termed quorum sensing (QS) in which they secrete chemical signal molecules, termed autoinducers, into their surrounding environment. The concentration of these signal molecules increases locally as a result of increasing cell density, and upon reaching a threshold level (when the population is 'quorate') the population activates a coordinated cellular response such as the production of virulence factors and growth as a biofilm community.

Pseudomonas aeruginosa (or simply P. aeruginosa) is a ubiquitous Gram-negative bacteria that is responsible for many opportunistic and nosocomial infections and chronic infection by P. aeruginosa is the leading cause of death of cystic fibrosis patients. P. aeruginosa has three main QS systems. The first two QS systems, LasR-LasI and RhlR-RhlI, are based on the LuxR-LuxI homologues of Vibrio fischeri, which makes use of acyl homoserine lactone (AHLs) as signal molecules. The AHL synthases are LasI and RhlI, which produce N-(3-oxododecanoyl)-L-homoserine lactone (OdDHL) and N-butanoylhomoserine lactone (BHL), respectively. The receptor for OdDHL is the LasR protein, while the receptor for BHL is the RhlR protein.

Together, the las and rhl QS systems regulate a host of virulence factors such as exoproteases (an example being elastase), siderophores, and toxins. The third signaling system utilizes another kind of signal molecule, 2-heptyl-3-hydroxy-4-quinolone, that has been termed the Pseudomonas quinolone signal (PQS) and is able to affect the expression of Las and Rhl-controlled genes. LasR is an attractive target for QS inhibition as LasR controls the other QS circuits (namely Rhl and PQS) within the P. aeruginosa hierarchy. The las and rhl systems are at the top and bottom of the hierarchy respectively, while the PQS system intervenes between them.

As QS controls the expression of multiple virulence factors in different bacteria, blocking of QS would be vital in attenuating the virulence of pathogenic bacteria. During the last decade, the QS system has been proposed as a target for developing next generation antimicrobial agents. The rationale for interrupting bacterial communication rather than inhibiting growth is because QS inhibitors (for short, QSIs), by targeting non-essential processes, are shown to not exert strong selective pressure for the evolution of resistance mechanisms as compared to the conventional growth-inhibitory compounds.

The conventional approach to identify QSIs is by using biosensor systems which often fuse a QS-regulated promoter to the lux, gfp or lacZ reporter genes. A wide range of QSIs was identified by the use of these biosensor systems. However, QSIs identified through the use of biosensors might not be target-specific and have some potential risk in their application. QS regulation is integrated into the complex bacterial regulation networks which also include nucleotide signaling (e.g. cAMP and c-di-GMP), iron signaling, phosphate signaling, and so on. Thus, QSIs identified through the use of biosensor systems might actually target other regulators which may also affect QS. This brings the risk that these QSIs might be able to induce virulence factors regulated by other regulation networks even though they can inhibit QS.

In contrast to the conventional lab-based screens, some have utilized a computer-based approach to drug screening known as structure-based virtual screening (SB-VS). SB-VS can be defined as a method to computationally screen large compound libraries for molecules that bind targets of known structure, and then test experimentally those predicted to bind well. Recent successes of this approach include: inhibitors against the apoptosis regulator Bcl-2, Hsp90, G-protein coupled receptors and metalloenzymes.

With the recent availability of crystal structures of bacteria QS receptor proteins such as LasR of P. aeruginosa and TraR of Agrobacterium tumefaciens, SB-VS has become a viable option for QSI discovery.

SUMMARY

The present invention is based on the inventors' finding that certain small molecule compounds known as quorum sensing inhibitors (QSIs) have been shown to effectively block QS and subsequently attenuate the virulence of Pseudomonas aeruginosa as well as increase its susceptibility to both antibiotics and the immune system.

In a first aspect, there is disclosed a compound of Formula I or Formula II,

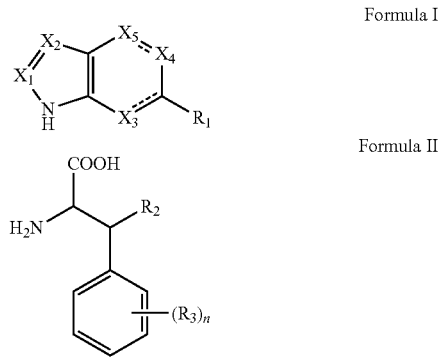

wherein
$R_1$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;
$R_2$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;
R and R' are independently selected from H and C1-C4 alkyl;
$X_1$ and $X_2$ are independently selected from the group consisting of N and $CR_4$;

R$_4$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;

X$_3$, X$_4$ and X$_5$ are independently selected from the group consisting of N, NH, CH and C(O);

R$_3$ if present is independently selected from the group consisting of halogen, hydroxyl, alkoxy, and C1-C4 alkyl;

n is 0, 1, 2, 3, 4, or 5;

the dashed lines represent a double bond that may be present or absent depending on the identity of X$_3$, X$_4$ and X$_5$.

In another aspect, use of the compound of the first aspect as a quorum sensing inhibitor for regulation of the quorum sensing system of microorganisms is disclosed.

In a further aspect, a pharmaceutical composition including a compound of the first aspect and a pharmaceutically acceptable excipient is disclosed.

In yet another aspect, a method for the treatment or prevention of bacterial damage or disease in a subject, the method including administering a therapeutically or prophylactically effective amount of a compound of the first aspect to said subject is disclosed.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

FIG. 11 shows a Table: List of *P. aeruginosa* and *E. coli* strains used in the present disclosure.

FIG. 12 shows a Table: Key residues within the LasR ligand binding pocket having hydrogen bonding interactions with OdDHL and the corresponding 5 QSI molecules.

FIG. 13 shows a Table: Proteins whose abundance in the *P. aeruginosa* PAO1 strain decreased significantly upon 5-imino-4,6-dihydro-3H-1,2,3-triazolo[5,4-d]pyrimidin-7-one (G1) addition. Significance was defined as a 115:114 abundance<0.66, p-value 115:114<0.05).

FIG. 14 shows a Table: Structures and docking scores of reference compounds.

FIG. 15 shows a Table: Structures and docking scores of twenty-two top-scoring compounds with the following selection criteria: Molecular weight below 200 Daltons, (docking) rerank score below −60. Ligand efficiency is computed as rerank score divided by the number of heavy atoms present in the compound.

FIG. 16 shows a Table: Parameters used for the import of molecules, template creation and docking in Molegro Virtual Docker.

DESCRIPTION

Figure 1:
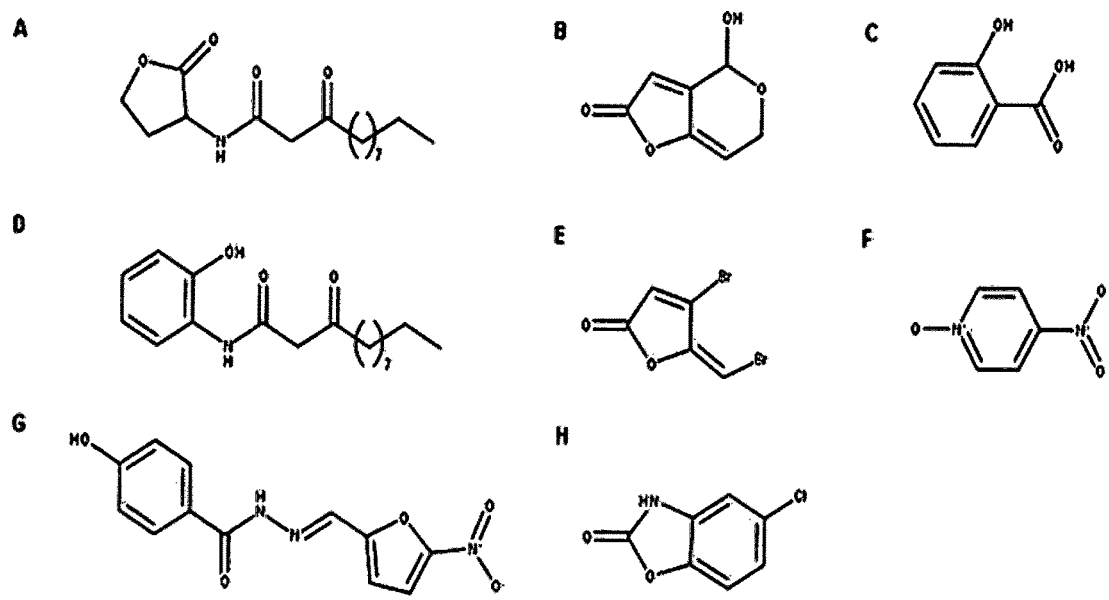
FIG. 1 shows the chemical structures of the reference ligand, OdDHL, and other known QS inhibitors used as comparisons for present structure-based virtual screening: (A) 3-Oxo-C12-HSL (OdDHL); (B) Patulin; (C) Salicylic acid; (D) 3-Oxo-C12-(2-aminophenol); (E) Furanone C30; (F) 4-Nitropyridine-N-oxide; (G) Nifuroxazide; and (H) Chlorzoxazone.

The following detailed description refers to the accompanying drawings that show, by way of illustration, specific details and embodiments in which the invention may be practiced. These embodiments are described in sufficient detail to enable those skilled in the art to practise the invention. Other embodiments may be utilized and chemical and other changes may be made without departing from the scope of the invention. The various embodiments are not necessarily mutually exclusive, as some embodiments can be combined with one or more other embodiments to form new embodiments.

*Pseudomonas aeruginosa* forms infectious biofilms on surfaces, for example, as diverse as cystic fibrosis lung tissue, contact lenses, and catheter tubes. Since bio film formation of *P. aeruginosa* has been demonstrated to require an AHL signaling system, inhibition of its quorum sensing system would result in an impaired ability to form biofilms and therefore in an increased susceptibility to antibacterial treatment.

The discovery that a wide spectrum of organisms use quorum sensing to control virulence factor production and other phenotypes such as biofilm formation makes it an attractive target for antimicrobial therapy. Pathogenic organisms using this signaling system to control virulence could potentially be rendered avirulent by blocking this cell-cell communication system. In contrast to traditional antibiotics, the risk of resistance development seems to be very low, since quorum sensing blocking agents or inhibitors (QSIs) would not kill the organism but disturb signal transduction pathways.

To this end, a computer-aided method for the rational identification of QSIs may provide a means of discovering QSIs with increased target specificity. In particular, use of a computer-aided approach for the discovery of novel QSIs of the *P. aeruginosa* LasR protein was investigated. The DG-AMMOS program was used to convert 2D chemical structures into 3-dimensional (3D) conformations based on distance geometry. The entire library of compounds from TimTec's Natural Derivatives Library, 3040 in all, was converted using DG-AMMOS to 3D structures, and then used for the molecular docking process within the Molegro Virtual Docker (MVD) program. In various embodiments, 22 small molecule QSI candidates were ordered and tested for its quorum sensing inhibition efficacy. Five of these compounds were found to inhibit the *P. aeruginosa* LasR QS system, in a dose-dependent manner, while only one compound, 5-imino-4,6-dihydro-3H-1,2,3-triazolo[5,4-d]pyrimidin-7-one (G1) was found to inhibit LasR specifically in an heterologous *E. coli* reporter strain. iTRAQ-based proteomic analysis was then used to study the protein expression changes in *P. aeruginosa* PAO1 as a result of G1 addition.

Accordingly, in a first aspect of the invention, there is provided a compound of Formula I or Formula II,

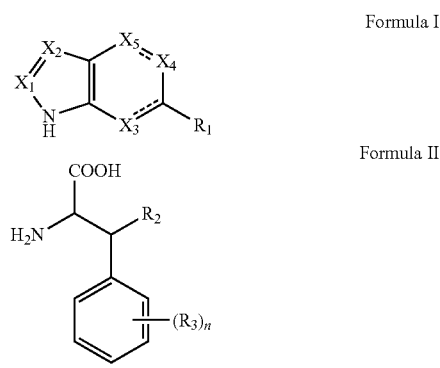

wherein
$R_1$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;

$R_2$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;

R and R' are independently selected from H and C1-C4 alkyl;

$X_1$ and $X_2$ are independently selected from the group consisting of N and CR$_4$;

$R_4$ is selected from the group consisting of H, halogen, C1-C4 alkyl, C2-C4 alkenyl, C2-C4 alkynyl, —C(O)—R, —NRR', —NR, —OR, —SR, —COOR, —CN, —NO$_2$, —C(O)—NRR', —NR'—C(O)—R, —SO$_2$—R and —(SO$_2$)—OR;

$X_3$, $X_4$ and $X_5$ are independently selected from the group consisting of N, NH, CH and C(O);

$R_3$ if present is independently selected from the group consisting of halogen, hydroxyl, alkoxy, and C1-C4 alkyl;

n is 0, 1, 2, 3, 4, or 5;

the dashed lines represent a double bond that may be present or absent depending on the identity of $X_3$, $X_4$ and $X_5$.

In the present context, the term "optionally substituted" or "substituted or unsubstituted" refers to a group in which none, one, or more than one of the hydrogen atoms have been replaced with one or more groups such as, but are not limited to, alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups. In embodiments in which two or more hydrogen atoms have been substituted, the substituent groups may be linked to form a ring.

In the present context, the term "aliphatic", alone or in combination, refers to a straight chain or branched chain hydrocarbon comprising at least one carbon atom. Aliphatics include alkyls, alkenyls, and alkynyls. Aliphatics include, but are not limited to, methyl, ethyl, propyl, isopropyl, butyl, isobutyl, tert.-butyl, pentyl, hexyl, ethenyl, propenyl, butenyl, ethynyl, butynyl, propynyl, and the like, each of which may be optionally substituted.

In the present context, the term "alkyl", alone or in combination, refers to a fully saturated aliphatic hydrocarbon. In certain embodiments, alkyls are optionally substituted. In certain embodiments, an alkyl comprises 1 to 10 carbon atoms, for example 1 to 4 carbon atoms, wherein (whenever it appears herein in any of the definitions given below) a numerical range, such as "1 to 4" or "C1-C4", refers to each integer in the given range, e.g. "C1-C4 alkyl" means that an alkyl group comprising only 1 carbon atom, 2 carbon atoms, 3 carbon atoms, or 4 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like.

In the present context, the term "alkenyl", alone or in combination, refers to an aliphatic hydrocarbon having one or more carbon-carbon double-bonds, such as two or three carbon-carbon double-bonds. In certain embodiments, alkenyls are optionally substituted, i.e. substituted or unsubstituted. In certain embodiments, an alkenyl comprises 2 to 15 carbon atoms, for example 2 to 4 carbon atoms. "C2-C4 alkenyl" means that an alkenyl group comprising only 2 carbon atoms, 3 carbon atoms, or 4 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like.

In the present context, the term "alkynyl", alone or in combination, refers to an aliphatic hydrocarbon having one or more carbon-carbon triple-bonds, such as two or three carbon-carbon triple-bonds. In certain embodiments, alkynyls are optionally substituted, i.e. substituted or unsubstituted. In certain embodiments, an alkynyl comprises 2 to 15 carbon atoms, for example 2 to 4 carbon atoms. "C2-C4 alkynyl" means that an alkynyl group comprising only 2 carbon atoms, 3 carbon atoms, or 4 carbon atoms. Examples of alkynyls include, but are not limited to, ethynyl, propynyl, butynyl, and the like.

In the present context, the term "halogen", or "halo" for short, refers to fluorine (F), chlorine (Cl), bromine (Br) or iodine (I).

In the present context, the term "heteroatom" refers to an atom other than carbon or hydrogen. Heteroatoms are typically independently selected from oxygen (O), sulfur (S), nitrogen (N), and phosphorus (P), but are not limited to those atoms. In embodiments in which two or more heteroatoms are present, the two or more heteroatoms may all be the same as one another, or some or all of the two or more heteroatoms may each be different from the others.

In the present context, the term "oxo" refers to a carbonyl (—C(O)) functional group.

In various embodiments, in Formula I $R_1$ may be NR. In certain cases, $R_1$ may be NH. In other cases, $R_1$ may be H.

In various embodiments, in Formula I $X_1$ and $X_2$ may be both same and are N.

In alternative embodiments, in Formula I $X_1$ and $X_2$ may be $CR_4$. In certain cases, $X_1$ is CH and $X_2$ is C—COOR or C—COOH.

In various embodiments, in Formula I $X_5$ may be C(O).

In one embodiment, the compound of Formula I is

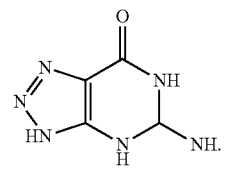

In another embodiment, the compound of Formula I is

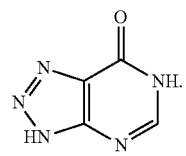

In yet another embodiment, the compound of Formula I is

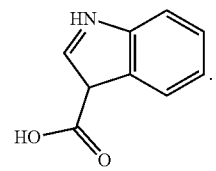

In various embodiments, in Formula II $R_2$ may be H or OR. In certain cases, in formula II $R_2$ may be OH.

In various embodiments, $R_3$ in Formula II may be absent, i.e. n is 0.

In other embodiments, $R_3$ in Formula II may be present and may be 1. For example, $R_3$ may be a halogen such as F.

In one embodiment, the compound of Formula II is

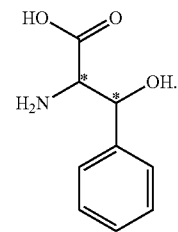 [SMILES: NC(C(=O)O)C(O)c1ccccc1]

In another embodiment, the compound of Formula II is

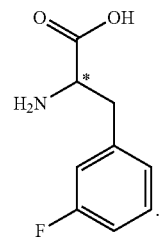

The compounds of Formula I or Formula II can be used as a quorum sensing inhibitor for regulation of the quorum sensing system of microorganisms, such as *P. aeruginosa*, to inhibit quorum sensing signaling of bacteria employing AHLs as signal molecules for cell-cell communication. In the following it is explained that the compounds of the present invention can be used as antibacterial agents in various applications.

In various embodiments, the compounds of Formula I or Formula II are useful for the treatment of a variety of human, animal and plant diseases, where bacterial pathogens regulate the expression of virulence genes and other phenotypes, e.g. bio film formation, through an AHL-based quorum sensing system. Furthermore, as the list of organisms employing quorum sensing signaling for their virulence continues to increase, the compounds of the invention can be used also for organisms which will be added to the above listed in future.

In various embodiments, the compounds are useful for the treatment of mammalian in particular human diseases caused by bacteria through the inhibition of the bacterial quorum sensing cascade rendering the pathogen avirulent. Such diseases include endocarditis, respiratory and pulmonary infections (preferably in immunocompromised and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*.

In general, the present invention provides a method for reducing the virulence of bacterial pathogens employing an AHL-based signaling system. In a preferred form, a method is provided to remove, diminish, detach or disperse a bacterial bio film from a living or nonliving surface by treating the surface with a compound of Formula I or Formula II. This method is also useful to prevent biofilm formation on a living or nonliving surface by treating the surface with a compound of Formula I or Formula II before bacterial colonization can initialize. The term "biofilm" refers to cell aggregations comprising either a single type of organism or a mixture of more than one organism, then referred to as "mixed biofilms". It is clear to persons skilled in the art, that the compounds of the present invention can be applied in a wide variety of different fields such as environmental, industrial and medical applications in order to prevent and/or treat damages or diseases caused by bacteria.

In various embodiments, the compounds of Formula I or Formula II can be used for various kinds of surfaces in private and public areas, where it is beneficial to inhibit quorum sensing systems of Gram-negative bacteria in order to prevent and/or treat colonization and biofilm formation. The compound is preferably applied to the surface as a solution of the compound, alone or together with other materials such as conventional surfactants, preferably sodium dodecyl sulfate, or detergents, biocides, fungicides, antibiotics, pH regulators, perfumes, dyes or colorants. In combination with a bacteriocidal agent, e.g., the compounds of Formula I or Formula II inhibit virulence or bio film formation whilst the bacteriocidal agent kills the pathogens.

In one embodiment, the compounds can be used as antibacterial agent for topical use in cleaning and treatment solutions such as disinfectants, detergents, household cleaner and washing powder formulations in the form of a spray or a dispensable liquid. In a preferred form, these solutions can be applied to windows, floors, clothes, kitchen and bathroom surfaces and other surfaces in the area of food preparation and personal hygiene. In addition, the compounds of Formula I or Formula II can be used as antibacterial ingredients in personal hygiene articles, toiletries and cosmetics such as dentifrices, mouthwashes, soaps, shampoos, shower gels, ointments, creams, lotions, deodorants and disinfectants and storage solutions for contact lenses.

In another embodiment, the compounds can be used to prevent or treat bacterial biofilms in industrial settings such as ship hulls, paper manufacturing, oil recovery and food processing. The compounds can also be applied to water processing plants or drinking water distribution systems where the colonized surface (preferably by *Pseudomonas aeruginosa*) is preferably the inside of an aqueous liquid system such as water pipes, water injection jets, heat exchangers and cooling towers. Until now biocides are the preferred tools to encounter these problems, but since biocides do not have a high specificity for bacteria, they are often toxic to humans as well. This can be circumvented by the application of the compounds of the present invention.

In a further embodiment, the present invention relates to a method of inhibiting and/or preventing medical device-associated bacterial infections. The invention provides articles coated and/or impregnated with a compound of Formula I or Formula II in order to inhibit and/or prevent biofilm formation thereon. The articles are preferably surgical instruments, blood bag systems or medical devices; more preferably either permanently implanted devices such as artificial heart valve, prostethic joint, voice prosthesis, stent, shunt or not permanently implanted devices such as endotracheal or gastrointestinal tube, pacemaker, surgical pin or indwelling catheter.

In a more preferred form, the indwelling catheters are urinary catheters, vascular catheters, peritoneal dialysis catheter, central venous catheters and needleless connectors. The catheter materials can be polyvinylchloride, polyethylene, latex, teflon or similar polymeric materials, but preferably polyurethane and silicone or a mixture thereof. In order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Furthermore, collection bags or layers sandwiched between an external surface sheath and a luminal silicone sheath have been constructed to overcome rapid loss of antimicrobial activity. Nevertheless, the emerging risk of bacterial resistance against traditional antibiotics limits the routine use of antibiotic-coated catheters.

The compounds of the present invention, however, offer the possibility to effectively reduce catheter-related bacterial infections with a low risk of resistance development due to a novel therapeutic strategy targeting highly sensitive signal transduction mechanisms in bacteria. The preferred form of application is the coating and/or impregnating of catheter materials on both the inner and outer catheter surfaces. More preferably, the compounds of Formula I or Formula II can be included in a mixture of antibacterial agents released continuously from a catheter-associated depot into the environment.

In another aspect, a pharmaceutical composition including a compound of Formula I or Formula II and a pharmaceutically acceptable excipient is disclosed.

In the present context, a "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils and polyethylene glycols.

Thus, the present invention also relates to compositions including pharmaceutical compositions comprising a therapeutically effective amount of a compound of any one of the compounds mentioned herein. As used herein a compound will be therapeutically effective if it is able to affect the target microorganism concentration within a cell. Preferably, a compound will be therapeutically effective if it is able to affect the target microorganism concentration within a cell where it is able to treat or prevent a bacteria-related disease or disorder in a subject after the compound has been administered to a subject.

In a further embodiment, the compounds of the present invention and their pharmacologically acceptable salts can be administered directly to animals, preferably to mammals, and in particular to humans as antibiotics per se, as mixtures with one another or in the form of pharmaceutical preparations which allow enteral or parenteral use and which as active constituent contain an effective dose of at least one compound of the Formula I or Formula II, or a respective salt thereof, in addition to customary pharmaceutical excipients and additives. The compounds of Formula I or Formula II can also be administered in form of their salts, which are obtainable by reacting the respective compounds with physiologically acceptable acids and bases.

The therapeutics can be administered orally, e.g., in the form of pills, tablets, coated tablets, sugar coated tablets, lozenges, hard and soft gelatin capsules, solutions, syrups, emulsions or suspensions or as aerosol mixtures. Administration, however, can also be carried out rectally, e.g., in the form of suppositories, or parenterally, e.g., in the form of injections or infusions, or percutaneously, e.g., in the form of ointments, creams or tinctures.

As mentioned above, in addition to the active compounds of Formula I or Formula II, the pharmaceutical composition can contain further customary, usually inert carrier materials or excipients. Thus, the pharmaceutical preparations can also contain additives or adjuvants commonly used in galenic formulations, such as, e.g., fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for modifying the osmotic pressure, coating agents or antioxidants. They can also contain two or more compounds of the Formula I and/or Formula II or their pharmacologically acceptable salts and also other therapeutically active substances.

Thus, the compounds of the present invention can be used alone, in combination with other compounds of this invention or in combination with other active compounds, for example with active ingredients already known for the treatment of the afore mentioned diseases, whereby in the latter case a favorable additive effect is noticed. Suitable amounts to be administered to mammalian in particular humans can range from 5 to 1000 mg.

To prepare the pharmaceutical preparations, pharmaceutically inert inorganic or organic excipients can be used. To prepare pills, tablets, coated tablets and hard gelatin capsules, e.g., lactose, corn starch or derivatives thereof, talc, stearic acid or its salts, etc. can be used. Excipients for soft gelatin capsules and suppositories are, e.g., fats, waxes, semi-solid and liquid polyols, natural or hardened oils etc. Suitable excipients for the production of solutions and syrups are, e.g., water, alcohol, sucrose, invert sugar, glucose, polyols etc. Suitable excipients for the production of injection solutions are, e.g., water, alcohol, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 0.1 to 100 mg/kg animal body weight preferably 1 to 50 mg/kg. Suitable dosage rates for larger mammals, e.g., humans, are of the order of from about 10 mg to 3 g/day, conveniently administered once, in divided doses 2 to 4 times a day, or in sustained release form.

In general, a daily dose of approximately 0.1 mg to 5000 mg, preferably 10 to 500 mg, per mammalian in particular human individual is appropriate in the case of the oral administration which is the preferred form of administration according to the invention. In the case of other administration forms too, the daily dose is in similar ranges. The compounds of Formula I or Formula II can also be used in the form of a precursor (prodrug) or a suitably modified form, that releases the active compound in vivo.

In a further embodiment, the compounds of the present invention can be used as pharmacologically active components or ingredients of medical devices, instruments and articles with an effective dose of at least one compound of the Formula I or Formula II or a respective salt thereof. The amount of the compounds used to coat for example medical device surfaces varies to some extent with the coating method and the application field. In general, however, the concentration range from about 0.01 mg per $cm^2$ to about 100 mg per $cm^2$. In a similar way the amount of the compounds has to be adjusted to the application mode if the compounds of the invention are used as components or ingredients in cleaning or treatment solutions. In general, effective dosages range from about 0.1 μM to about 1000 mM.

In yet another aspect, a method for the treatment or prevention of bacterial damage or disease in a subject, the method including administering a therapeutically or prophylactically effective amount of a compound of the first aspect to said subject is disclosed.

Subject, for the purposes of the present invention includes humans and other animals, particularly mammals. Thus the methods are applicable to both human therapy and veterinary applications. In certain embodiments the subject is a mammal, and in a preferred embodiment the subject is human.

"Treatment" and "treat" and synonyms thereof refer to both therapeutic treatment and prophylactic or preventative measures, wherein the object is to prevent or slow down (lessen) bacterial damage or disease in a subject.

As used herein, in the context of a treatment or prevention of a bacterial damage or disease, a "therapeutically effective amount" or "prophylactically effective amount" of a compound will be an amount of active agent that is capable of treating, preventing or at least slowing down (lessening) bacterial damage or disease in a subject. Dosages and administration of an antagonist of the invention in a pharmaceutical composition may be determined by one of ordinary skill in the art of clinical pharmacology or pharmacokinetics. An effective amount of the compound or composition to be employed therapeutically will depend, for example, upon the therapeutic objectives, the route of administration, and the condition of the mammal, as described above. Accordingly, it will be necessary for the therapist to titer, the dosage and modify the route of administration as required to obtain the optimal therapeutic effect.

In summary, a structure-based virtual screening (SB-VS) approach was used for the discovery of novel QSI candidates. Three-dimensional structures of 3,040 natural compounds and their derivatives were obtained, after which molecular docking was performed using the QS receptor LasR as a target. Based on docking scores and molecular weight, compounds were purchased to determine their efficacy as quorum sensing inhibitors. Using a live reporter assay for quorum sensing, various compounds were found to be able to inhibit QS regulated gene expression in *P. aeruginosa* in a dose-dependent manner. The most promising compound, G1 (see example section below), was evaluated by iTRAQ-based proteomic analysis and it was found to significantly affect the abundance of 46 proteins (19 were up-regulated, 27 were down-regulated) in *P. aeruginosa* PAO1. It specifically reduced the expression of several quorum-sensing regulated virulence factors such as protease IV, chitinase and pyoverdinesynthetases. G1 was also able to reduce extracellular DNA release and inhibited the secretion of the virulence factor, elastase, whose expression is regulated by LasR. These results demonstrate the utility of SB-VS for the discovery of target-specific QSIs.

In order that the invention may be readily understood and put into practical effect, particular embodiments will now be described by way of the following non-limiting examples.

EXAMPLES

Materials and Methods

Structure-based virtual screening. The process workflow for the structure-based virtual screening is based largely on the methods used previously (Yang et al. 2009 *Computer-aided identification of recognized drugs as Pseudomonas aeruginosa quorum-sensing inhibitors, Antimicrob Agents Chemother* 53:2432-244327), with the major difference being the usage of DG-AMMOS for the conversion of the entire compound library into 3-D structures.

Protein structure file and ligand database. The X-ray crystal structure of the *P. aeruginosa* LasR ligand-binding domain (LBD) bound to its natural ligand, OdDHL, was downloaded from the Protein Data Bank website (PDB ID: 2UV0) and used for structure-based virtual screening. For the SB-VS, the structures of 3040 ligands from TimTec's (TimTec LLC, Newark, Del.; http://www.timtec.net) Natural Derivatives Library were downloaded from Timtec's website (http://www.timtec.net/NDL-3000-Natural-Derivatives-Library.html). These structures were in 2D coordinate structure-data file (SDF) format, hence, an automated program, DG-AMMOS (Lagorce et al. 2009. *DG-AMMOS: A New tool to generate 3D conformation of small molecules using Distance Geometry and Automated Molecular Mechanics Optimization for in silico Screening. BMC Chem Biol* 9:6) was used to convert the entire library of 2D chemical structures into 3-dimensional (3D) conformations based on distance geometry and automated molecular mechanics optimization. Thus, the entire library of compounds from TimTec's Natural Derivatives Library, 3040 in all, was converted to 3D structures and used for the subsequent molecular docking procedures. 2D structures of reference compounds were drawn manually in MarvinSketchver 5.9.0 (ChemAxon Ltd., Hungary) and then saved as 2D SDF files. The SDF files were merged into a single SDF file using OpenBabel ver. 2.3.1 (OpenEye Scientific Software) and like-wise converted to 3D structures through the use of DG-AMMOS.

Molecular docking. The Molegro Virtual Docker (MVD) Ver 5.0.0 program (Molegro Aps., Denmark) was used for the automated docking procedure. MVD uses the MOLDOCK algorithm which was able to correctly identify the binding mode of ligands with 87% accuracy which was higher than that of the modern docking programs GLIDE and Surflex. From the LasR PDB structure file, only the E monomer LBD in a complex with the OdDHL ligand, OHN 1169 [E], was imported into the MVD workspace. Water molecules were not imported, and default parameters were used for the import process.

For the docking process, a docking template was first generated based on the interaction of the native OdDHL ligand with the LasR ligand-binding domain. This template included steric, hydrogen donor, hydrogen acceptor and ring contributions. Template docking was then carried out using Ligand Evaluator for scoring of the poses and Moldock Optimizer for the search algorithm. The docking was constrained to a sphere of 9 Å radius centered on the OdDHL ligand and its corresponding cavity. For molecular docking, 3040 ligands from the Natural Derivative Library and 7 reference ligands (OdDHL reference ligand along with 7 known QSIs) were used. Each compound was docked for 10 iterations in order to obtain an energy-minimized protein-ligand conformation. One pose was generated by each run, and the resulting poses were ranked. The parameters used for import of molecules and docking in MVD are specified in FIG. 16. The program LIGPLOT ver 4.5.3 (Wallace et al. 1995. *LIGPLOT: a program to generate schematic diagrams of protein-ligand interactions. Protein Eng* 8:127-134) was used to map the interactions between QSI lead compounds and the residues within the LasR protein LBD. PyMOLver 1.4 (Schrodinger, LLC) was used for preparation of 3D images.

Selection of QSI Candidates. Compounds from the TimTec Natural Derivative Library were docked against the LasR LBD in MVD and subsequently ranked according to their rerank score, molecular weight in Daltons (Da), and the calculated ligand efficiency (computed as Rerank Score divided by the number of heavy atoms in a compound). In order to select for small molecule QSI candidates, only compounds having a molecular weight less than 200 Da and a rerank score below −60 were selected. The rerank score value of −60 used as a cut-off because known QSIs that were docked in MVD generally had a score below −60. A total of 22 QSI candidates were selected, and were purchased from TimTec, Inc. (TimTec LLC, Newark, Del.; http://www.timtec.net). Compounds were shipped in glass vials in powder form, and these were dissolved in DMSO prior to in vitro experiments. The purity (>90%) and identity of all compounds were confirmed by HPLC-MS (ESI) on a Waters Aquity reverse-phase ultra-performance liquid chromatography (UPLC) system equipped with a diode array detector using an AQUITY UPLC BEH C18 column (d 1.7 µm, 2.1×50 mm; column temp: 65° C.; flow: 0:6 mL/min). Eluents A (0.1% $HCO_2H$ in $H_2O$) and B (0.1% $HCO_2H$ in MeCN) were used in a linear gradient (5% B to 100% B) in a total run time of 2.6 min. The LC system was coupled to a SQD mass spectrometer.

Bacterial strains. To determine the QSI activity of the compounds selected from the virtual screening, the following *P. aeruginosa* and *E. coli* monitor strains were used (FIG. 11). These monitor strains have their respective promoters fused to an unstable Gfp (green fluorescent protein) that has a C-terminal oligopeptide extension containing the amino acids ASV [gfp(ASV)]; this causes the Gfp protein to be more susceptible to degradation by housekeeping proteases and therefore have a short half-life. As such, unstable gfp(ASV) allows for monitoring of temporal QS-regulated gene expression. For proteomic analysis, the sequenced *P. aeruginosa* PAO1 wild-type strain obtained from the Pseudomonas Genetic Stock Center (www.pseudomonas.med.ecu.edu; PAO0001) was used.

Growth media and conditions. The bacteria strains were grown in either ABTGC or Luria-Bertani (LB) medium. ABTGC medium is a AB minimal medium containing 2.5 mg/L thiamine, supplemented with 0.2% (wt/vol) glucose and 0.2% (wt/vol) Casamino Acids. LB medium contains 1.0% tryptone, 0.5% yeast extract and 1.0% NaCl adjusted to pH7.0. Overnight cultures were grown for 16 h at 37° C. and shaken at 180 rpm. Selective media were supplemented with ampicillin (100 mg liter$^{-1}$) or gentamicin (60 mg liter$^{-1}$) where appropriate.

P. aeruginosa QS inhibition assays. Test compounds were dissolved in 100% DMSO and mixed with ABTGC media, after which they were added to the first column of wells of a 96-well microtitre plate (Nunc) to give a final concentration of 100 μM in a final volume of 200 μl. 100 μL of ABTGC media was then added to the remaining wells in the plate and serial two-fold dilutions of the inhibitors were done by adding 100 μL of the preceding inhibitor-containing well to the subsequent one. The final column was left without inhibitor as a control. Next, an overnight culture of P. aeruginosa lasB-gfp(ASV) strain, grown in LB medium at 37° C. with shaking, was diluted to an optical density (OD) at 600 nm of 0.2, and 100 μl of bacterial suspension was added to each well of the microtitre plate. Hence, inhibitor concentrations ranged from 50 μM to 0.78125 μM across the plate, in a volume of 200 μL. The microtitre plate was incubated at 37° C. in a Tecan Infinite 200 Pro plate reader (Tecan Group Ltd., Männedorf, Switzerland). GFP fluorescence (excitation at 485 nm, emission at 535 nm) and cell density ($OD_{600}$) measurements were collected at 15 min intervals for at least 14 h. The P. aeruginosa Rhl and Pqs inhibition assays were performed in a similar manner to the LasR inhibition assay.

E. coli Competition Assay between QSI compounds and OdDHL. The E. coli lasB-gfp(ASV) reporter strain was used for the competition assay, which was performed in a similar manner to the P. aeruginosa LasR inhibition assay. OdDHL and the QSI to be studied were added to the wells of a microtitre plate containing ABTGC media. Wells without OdDHL and/or QSI were included as controls. An overnight culture of E. coli lasB-gfp(ASV) strain, grown in LB medium at 37° C. with shaking, was diluted to an $OD_{600}$ of 0.2, and 100 μl of bacterial suspension was added to each well of the microtitre plate. Hence, the plate contained OdDHL at concentrations ranging from 20 nM to 320 nM, and QSI at concentrations ranging from 3.125 μM to 50 μM (including control wells without OdDHL, QSI or both). GFP and $OD_{600}$ readings were obtained as described above for the P. aeruginosa LasR inhibition assay.

Inhibition of the Rhl and PQS QS systems in wild-type PAO1 and PAO1 lasR mutant. Wild-type P. aeruginosa PAO1 strains harboring either the rhlA-gfp(ASV) reporter or the pqsA-gfp(ASV) reporter, and a P. aeruginosa PAO1 lasR mutant harboring either the rhlA-gfp(ASV) reporter or the pqsA-gfp(ASV) reporter were used for this experiment (Refer to FIG. 11 for strain information). Overnight cultures of these four strains were diluted 100-fold in ABTGC media within 96-well microtitre plates to a final volume of 200 μL per well. Each of the five QSIs was added in triplicate to a final concentration of 50 μM. 0.5% DMSO was used as a negative control. The microtitre plate was incubated at 37° C. in a Tecan Infinite 200 Pro plate reader where GFP and $OD_{600}$ readings were measured at 15 min intervals.

Glass Slide Biofilm Assay for Observation of eDNA Release. The glass slide biofilm assay was performed (Liu et al. 2010 *Synergistic activities of an efflux pump inhibitor and iron chelators against Pseudomonas aeruginosa growth and biofilm formation. Antimicrob Agents Chemother* 54:3960-3963). Briefly, gfp-tagged P. aeruginosa PAO1 biofilms were cultivated in 50 ml BD falcon tubes containing 15 ml ABTG medium. A sterile 24 mm×60 mm glass cover slide was inserted into each falcon tube for supporting biofilm growth. G1 (10 μm) was added into the biofilm medium to examine its impact on P. aeruginosa PAO1 biofilm formation. DMSO was added alone to the medium as control. Biofilms were incubated at 37° C. without shaking. 2 μM propidium iodide (Sigma-Aldrich) was added to biofilm cultures to stain extracellular DNA for 5 min after 24-hour growth. After that, biofilm attached glass slides were observed by confocal laser scanning microscopy (CLSM).

iTRAQ-Based Proteomics Analyses for G1. Isobaric tag for relative and absolute quantitation (iTRAQ)-based proteomic analysis was used to study the changes in protein expression of the P. aeruginosa PAO1 strain in response to the addition of 25 μM of G1. Proteomics experiments were performed at the Proteomic Core Facility of the Biological Research Center, School of Biological Sciences, Nanyang Technological University, Singapore. A full description of the proteomics workflow is given below.

Protein preparation and digestion. The P. aeruginosa PAO1 strain was grown in ABTG media. Sub-lethal concentrations of G1 (25 μM) were added to independent P. aeruginosa PAO1 cultures respectively. Cultures were grown in LB medium at 37° C. with shaking until late log phase (OD 600 nm=1.0) before harvesting. After harvesting, cell pellets were washed with 1×PBS and resuspended in 2 ml of lysis buffer containing 0.5M TEAB and 0.1M SDS. The cells were ruptured by sonication, and the cell debris was removed by centrifugation at 4° C. at 16000×g for 15 min. 200 μg of proteins from different growth conditions were dissolved in equal volume of sample buffer (Invitrogen) supplemented with 0.5% 2-mercaptoethanol and denatured by boiling at 95° C. for 5 min. 1D gel electrophoresis was carried out using 10% SDS-PAGE for in-gel digestion.

Proteins were first reduced using 5 mM Tris-(2-carboxyethyl)phosphine (TCEP) for 1 h at 60° C., followed by blocking of cysteine residues by 10 mM methyl methanethiosulfate (MMTS) for 30 min at room temperature in the dark. Trypsin was added at a ratio of 1:50 (trypsin/sample). It was then incubated at 37° C. overnight. The tryptic peptides were extracted by 50% ACN/5% Acetic Acid from gel for 3 times and were desalted using Sep-Pak C18 cartridges (Waters, Milford, Mass.) and dried in a SpeedVac (Thermo Electron, Waltham, Mass.). All chemicals were purchased from Sigma-Aldrich unless stated otherwise.

iTRAQ labeling. The iTRAQ labeling of the tryptic peptides was performed using 4-plex iTRAQ reagent kit (Applied Biosystems, Foster City, Calif.), according to the manufacturers protocol. 200 μg of peptides from each condition were individually labeled with respective isobaric tags: control sample with 114, and the G1 treated sample with 115. After 2 h incubation, the samples were quenched by water, desalted using C18 solid phase extraction cartridge, and then vacuum-centrifuged to dryness. The iTRAQ-labeled peptides were reconstituted in Buffer A (10 mM ammonium acetate, 85% acetonitrile, 0.1% formic acid) and fractionated using ERLIC column (200×4.6 mm, 5 μm particle size, 200 Å pore size) by HPLC system (Shimadzu, Japan) at a flow rate of 1.0 ml/min using a previously optimized protocol (Hao et al. 2010 *Novel application of electrostatic repulsion-hydrophilic interaction chromatography (ERLIC) in shotgun proteomics: comprehensive profiling of rat kidney proteome. J Proteome Res* 9:3520-3526).

The HPLC chromatograms were recorded at 280 nm and fractions were collected online using automated fraction collector. 20 fractions were collected and concentrated using vacuum centrifuge and reconstituted in 3% ACN with 0.1% formic acid for LC-MS/MS analysis.

LC-MS/MS. The peptides were separated and analyzed on a home-packed nanobore C18 column (15 cm×75 μm; Reprosil-Pur C18-AQ, 3 μm, Dr Maisch, Germany) with a Picofritnanospray tip (New Objectives, Woburn, Mass., USA) on a Tempo™ nano-MDLC system coupled with a QSTAR® Elite Hybrid LC-MS/MS system (Applied Biosystems). Peptides from each fraction were analyzed in triplicate by LC-MS/MS over a gradient of 90 min. The flow rate of the LC system was set to a constant 300 nl/min. Data acquisition in QSTAR Elite was set to positive ion mode using Analyst® QS 2.0 software (Applied Biosystems). MS data was acquired in positive ion mode with a mass range of 300-1600 m/z. Peptides with +2 to +4 charge states were selected for MS/MS. For each MS spectrum, the three most abundant peptides above a five-count threshold were selected for MS/MS and dynamically excluded for 30 s with a mass tolerance of 0.03 Da. Smart information-dependent acquisition was activated with automatic collision energy and automatic MS/MS accumulation. The fragment intensity multiplier was set to 20 and maximum accumulation time was 2 s.

Data analysis. Spectra acquired from the three technical replicates were submitted to ProteinPilot (v3.0.0.0, Applied Biosystems) for peak-list generation, protein identification and quantification. User defined parameters of the Paragon algorithm in ProteinPilot software were configured as follows: (i) Sample Type, iTRAQ2-plex (Peptide Labeled); (ii) Cysteine alkylation, MMTS; (iii) Digestion, Trypsin; (iv) Instrument, QSTAR Elite ESI; (v) Special factors, Urea denaturation; (vi) Species, None; (vii) Specify Processing, Quantitate & Bias Correction; (viii) ID Focus, biological modifications, amino acid substitutions; (ix) Database, *P. aeruginosa* PAO1; (x) Search effort, thorough ID; (xi) Result quality, Unused ProtScore(Conf) >0.05 (10.0%). Default precursor and MS/MS tolerance for QSTAR ESI MS instrument were adopted automatically by the software. For iTRAQ quantitation, the peptide for quantification was automatically selected by Pro Group algorithm to calculate the reporter peak area, error factor (EF) and p-value. The resulting data was auto bias-corrected by build-in Protein-Pilot algorithm to get rid of any variations imparted due to the unequal mixing during combining different labeled samples. During bias correction, the software identifies the median average protein ratio and corrects it to unity, and then applies this factor to all quantitation results. A strict cutoff of unused ProteinScore ≥2, which corresponds to a confidence limit of 99%, was considered for protein identifications and further analysis.

Elastase Assay. *P. aeruginosa* PAO1 wild-type and an elastase negative lasI rhlI mutant were cultivated in LB medium overnight at 37° C. with shaking. Overnight cultures were 1:100 diluted to 5 ml ABTGC medium and incubator at 37° C. with shaking. Compound G1 was supplemented into the PAO1 cultures at final concentrations of 0, 50, 100 μM respectively. After 2 h incubation, 0.8 mL culture supernatants were sampled by centrifugation (18000 g, 4 min) and filtration through 0.2 micron filters. Elastase activity of *P. aeruginosa* culture supernatants was measured by using The EnzChekElastase Assay Kit (Invitrogen), which uses BODIPY-FL-labeled DQ elastin conjugate as the substrate of elastase. The BODIPY-FL-labeled DQ elastins conjugate when cleaved by elastase enzyme, yields highly fluorescent fragments. Fluorescence was recorded every 6 min for 180 min by using a Tecan Infinite 200 Pro plate reader (excitation at 490 nm, emission at 520 nm).

Results

Structure-Based Virtual Screening for QSIs. Molecular docking was first performed using the reference ligand OdDHL and several known LasR inhibitors, against the ligand binding domain of LasR (PDB ID: 2UV0) in MVD. These compounds and their structures are shown in FIG. 1, and their docking scores (FIG. 14) provide a comparison for the selection of potential QSI candidates from the library compound screening.

A 3D structural database containing 3,040 structures of compounds from TimTec's Natural Derivatives Library was created using DG-AMMOS after which it was docked against the ligand binding domain of LasR. Twenty-two compounds having a rerank score below −60 and having a molecular weight less than 200 Da were selected as QSI candidates. These 22 structures are shown in FIG. 15. The cutoff value for the rerank score was set as −60 because most of the known QSIs that were docked earlier had scores below that value. The molecular weight cutoff value of 200 Da was arbitrarily determined in order to select for the most effective small molecule inhibitors that can easily penetrate the bacteria cell. Thus, the 22 compounds selected were obtained and tested for its inhibition in vitro.

Figure 2:
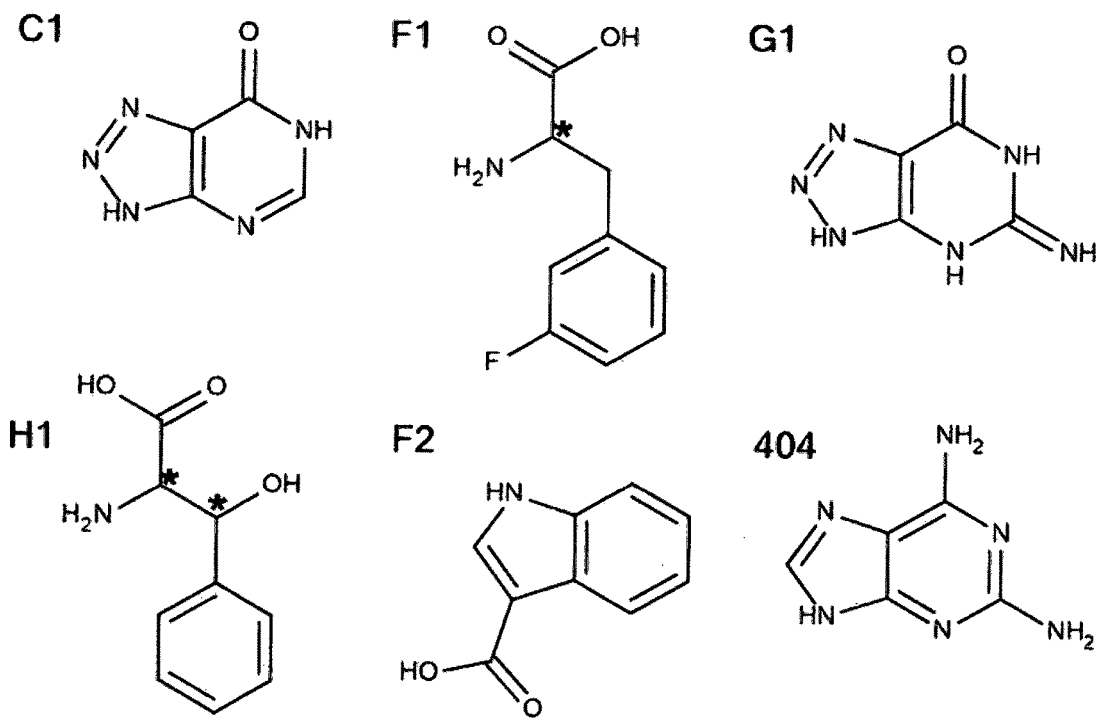
FIG. 2 shows the structures of five QSI candidates and an additional compound found to be structurally similar to C1 and G1. The five QSIs are: 6-hydro-3H-1,2,3-triazolo[5,4-d]pyrimidin-7-one (C1); 2-amino-3-(3-fluorophenyl)propanoic acid (F1); 5-imino-4,6-dihydro-3H-1,2,3-triazolo[5,4-d]pyrimidin-7-one (G1); 2-amino-3-hydroxy-3-phenylpropanoic acid (H1); and indole-3-carboxylic acid (F2). Compounds F1 and H1 are racemic, and asterisks within the structure denote the stereogenic centers within these compounds. Purine-2,6-diamine (404) was found through a structural similarity search of compounds with similar structure to G1.

Inhibition Assay with the *P. aeruginosa* lasB-gfp(ASV) strain. In the preliminary screen, the 22 selected QSI candidates were screened for their ability to inhibit QS-controlled green fluorescent protein (GFP) expression in the *P. aeruginosa* lasB-gfp(ASV) strain. Elastase (encoded by the lasB gene) is a virulence factor that is controlled by LasR and therefore a good indicator for LasR activity. Five compounds, code-named C1, F1, G1, H1 and F2, (FIG. 2) were found to inhibit LasR-controlled GFP expression in a dose-dependent manner without affecting cell growth. For ease of identification, each compound was designated a short compound identification code based on its well position in the shipment in place of its standard IUPAC name.

Figure 3:
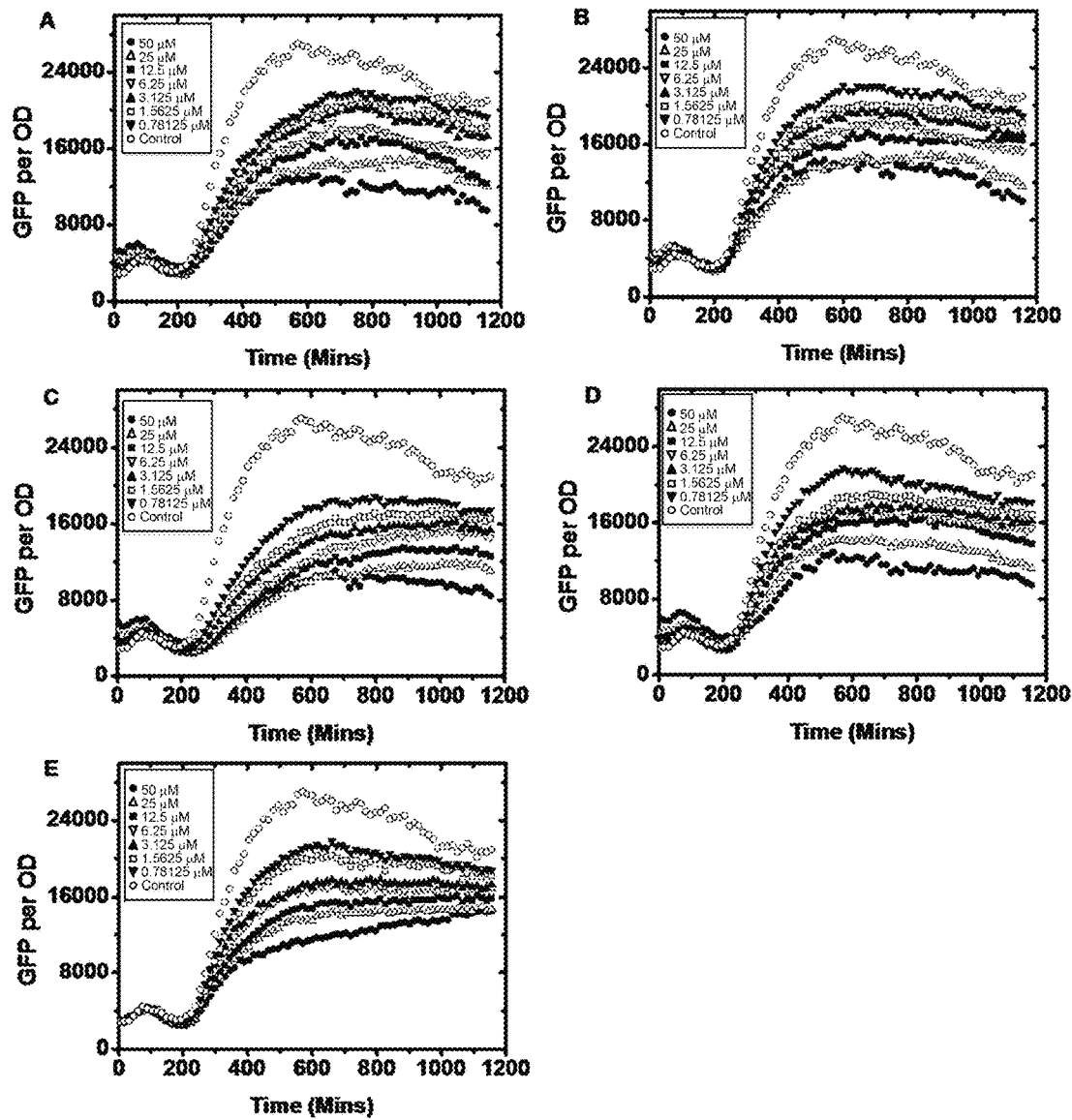
FIG. 3 shows dose-responses curves of (A) 6-hydro-3H-1,2,3-triazolo[5,4-d]pyrimidin-7-one (C1); (B) 2-amino-3-(3-fluorophenyl)propanoic acid (F1); (C) 5-imino-4,6-dihydro-3H-1,2,3-triazolo[5,4-d]pyrimidin-7-one (G1); (D) 2-amino-3-hydroxy-3-phenylpropanoic acid (H1); and (E) indole-3-carboxylic acid (F2) when incubated with the *P. aeruginosa* PAO1 lasB-gfp (ASV) strain. The legend shows the concentrations of the respective QSI used. The experiments were performed in triplicate; the figure shows a representative experiment.
Figure 4D:
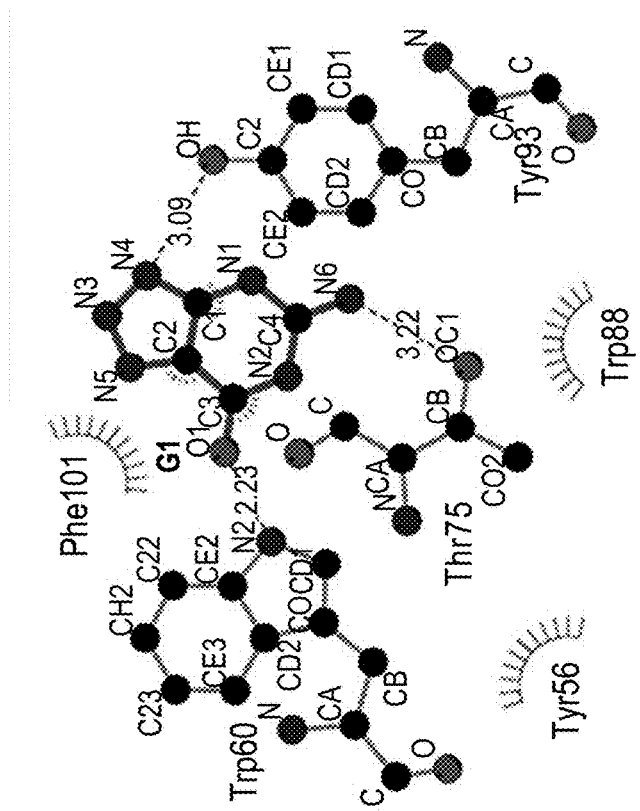
FIGS. 4 A-F shows interaction maps between residues within the LasR LBD and the following compounds: (A) the native acyl homoserine lactone ligand, OdDHL; (B) 6-hydro-3H-1,2,3-triazolo[5,4-d]pyrimidin-7-one (C1); (C) 2-amino-3-(3-fluorophenyl) propanoic acid (F1); (D) 5-imino-4,6-dihydro-3H-1,2,3-triazolo[5,4-d]pyrimidin-7-one (G1); (E) 2-amino-3-hydroxy-3-phenylpropanoic acid (H1); and (F) indole-3-carboxylic acid (F2).
Figure 4C:
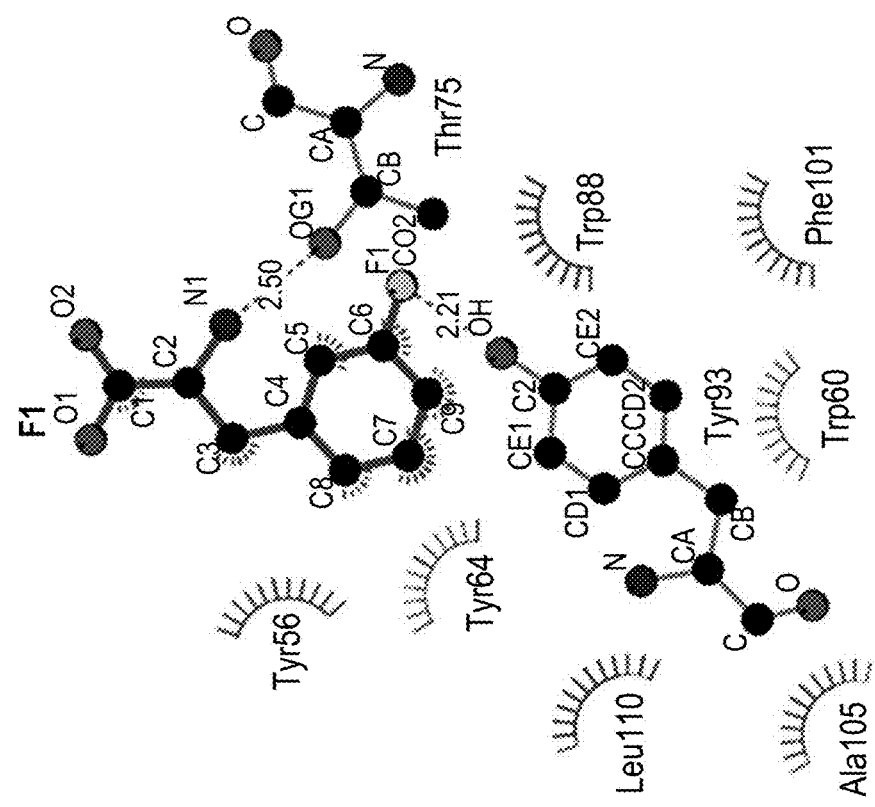
Figure 4F:
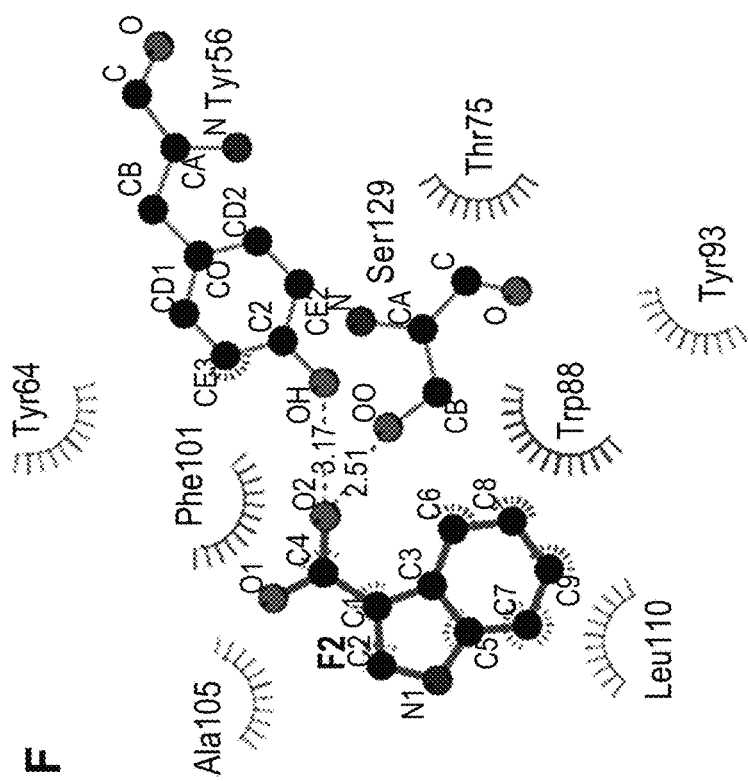
Figure 4E:
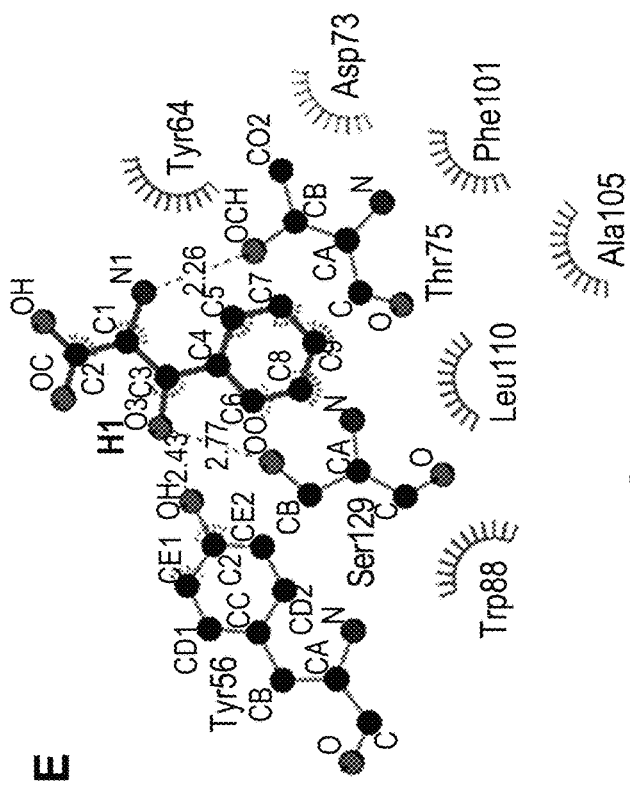

The dose-response curves of these 5 QSI candidates when incubated with the *P. aeruginosa* PAO1 lasB-gfp(ASV) strain are shown in FIG. 3. GFP expression, which was measured in relative fluorescence units, was normalized by dividing the GFP value by the corresponding $OD_{600}$ value measured at that time-point. 'Control' refers to the PAO1 strain grown without the presence of QSI, and as expected, it had the highest GFP per OD values. For these five compounds, dose-dependent inhibition of lasB-gfp expression was observed, i.e. the higher the concentration of QSI that was present, the greater the inhibition of gfp expression.

In order to map the interactions between the five QSI compounds and the residues within the LasR protein ligand-binding site, the program LIGPLOT ver 4.5.3 (FIGS. 4A-F) was used. This program provides a 2-dimensional map showing the hydrogen-bonding and hydrophobic interactions between atoms in the ligand and that of the binding partner. PyMOL was also used for 3D representations of these interaction maps (data not shown).

Figure 5:
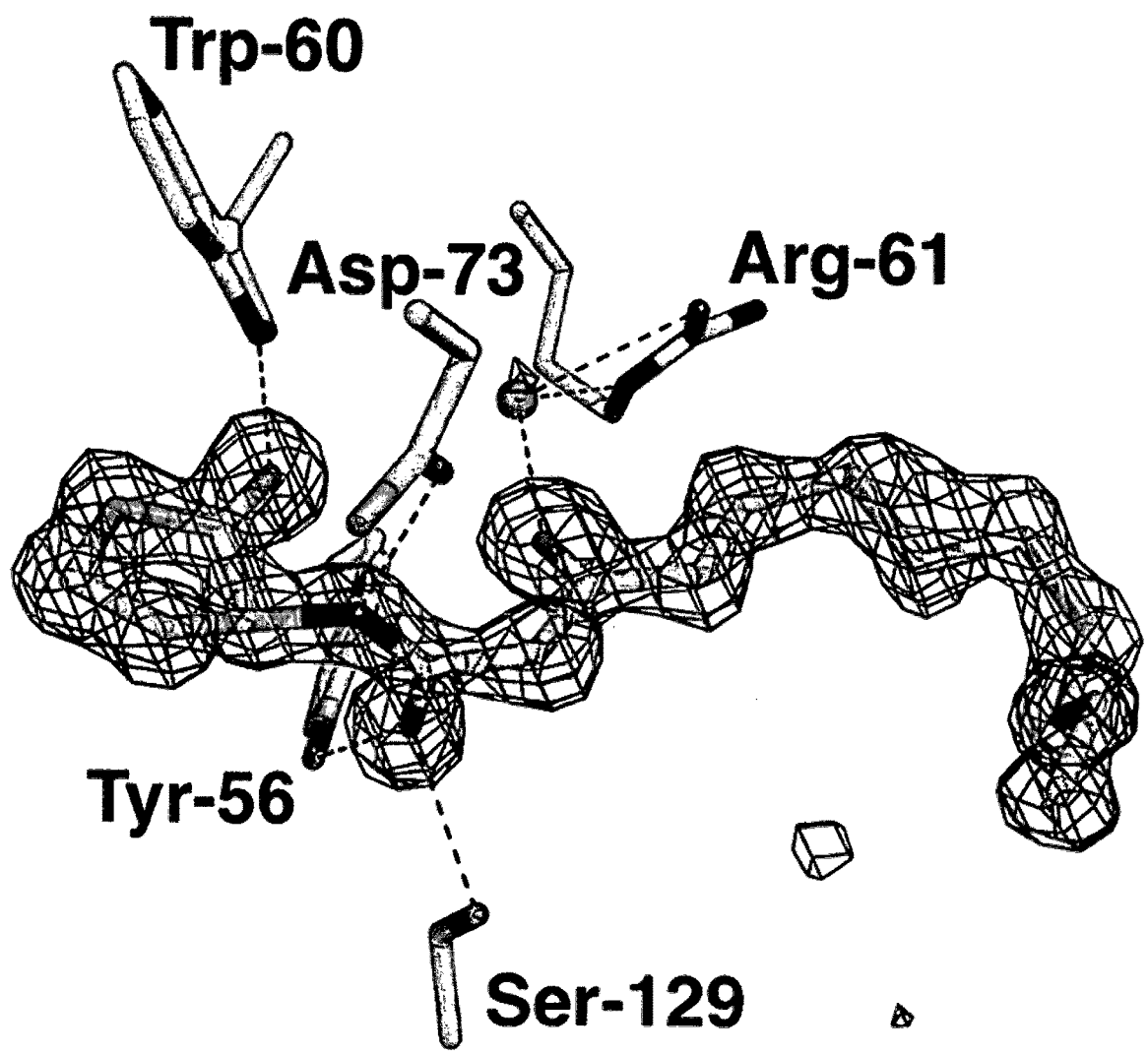
FIG. 5 shows a crystal structure model of the interactions between residues in the LasR ligand-binding pocket with the autoinducer molecule OdDHL. The wire mesh shows the electron density map. Image adapted from Zou et al. 2009. *Molecular Basis for the Recognition of Structurally Distinct Autoinducer Mimics by the Pseudomonas aeruginosa LasR Quorum-Sensing Signaling Receptor. Chem Biol* 16:961-970.

FIG. 12 summarizes the interactions between presently identified 5 QSI compounds and residues within the LasR ligand binding domain (LBD). In a recent study, the LasR was crystallized with OdDHL LBD and other AHL agonists which showed that LasR and OdDHL appeared to interact at residues Tyr 56, Trp 60, Arg 61, Asp 73 and Ser 129 (FIG. 5). Those results agree with the residues identified by LIGPLOT as determined in this study (FIG. 12).

Figure 6:
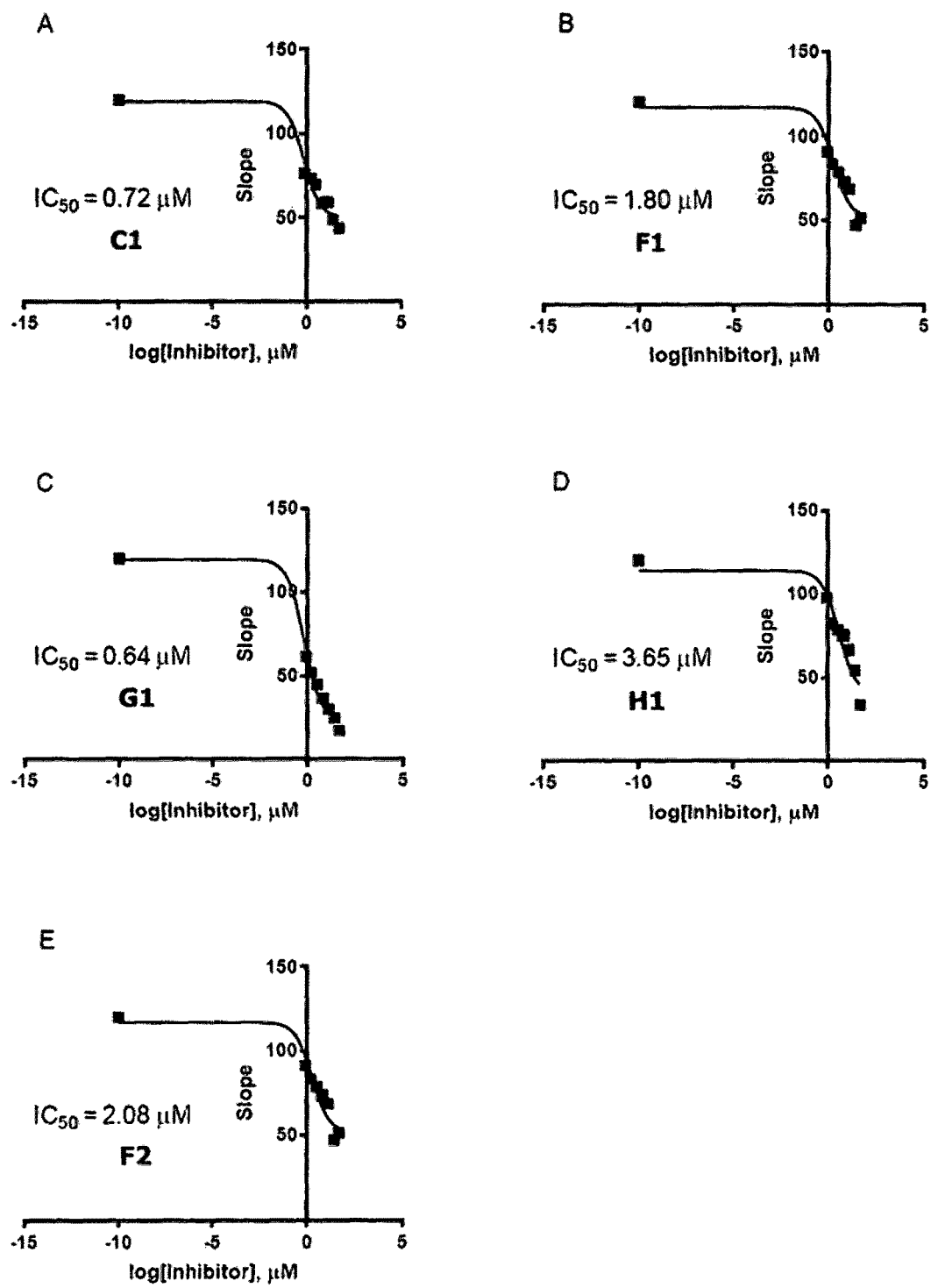
FIG. 6 shows the half maximal inhibitory concentration (IC$_{50}$) of (A) 6-hydro-3H-1,2,3-triazolo[5,4-d]pyrimidin-7-one (C1); (B) 2-amino-3-(3-fluorophenyl)propanoic acid (F1); (C) 5-imino-4,6-dihydro-3H-1,2,3-triazolo[5,4-d]pyrimidin-7-one (G1); (D) 2-amino-3-hydroxy-3-phenylpropanoic acid (H1); and (E) indole-3-carboxylic acid (F2). The minimum concentration of inhibitor was arbitrarily designated by the Graphpad PRISM software to have a log [inhibitor] value of −10 (log)μM, as the logarithm of zero is undefined.

IC$_{50}$ Value Comparisons of the Five QSI Candidates. The slope of the curve for each QSI was calculated based on its respective dose-response curves (from FIG. 3) and plotted against the log inhibitor concentration. The slope is indicative of the biosynthesis rate of GFP due to AHL induction. The half maximal inhibitory concentrations (IC$_{50}$) of the five QSI candidates were calculated using the Graphpad Prism 6 software package (GraphPad Software Inc., CA, USA). The IC$_{50}$ values of the 5 QSIs were mainly in the low micromolar range, with two compounds (C1 and G1) having values in the high nanomolar range (FIG. 6).

G1 had the lowest IC$_{50}$ value of 0.64 µM meaning that this inhibitor was able to inhibit lasB-gfp expression with high efficiency. However, these compounds were not necessarily interacting directly with LasR, and therefore the heterologous E. coli strain containing the lasB-gfp (ASV) reporter to test for LasR-specific inhibition was used.

AHL Competition Assay Using the Heterologous E. coli lasB-gfp (ASV) strain. The five QSI candidates were tested for their specificity in inhibiting the LasR receptor by incubating these QSIs with the E. coli lasB-gfp (ASV) reporter strain. LasR is under the control of the Lac promoter and is constitutively expressed, and only LasR can activate gfp expression in this system. P. aeruginosa-based QS systems do not exist in E. coli, so exogenous OdDHL has to be added. Hence this heterologous system provides a way to eliminate the contribution of QSI interaction with higher levels of control.

Figure 7:
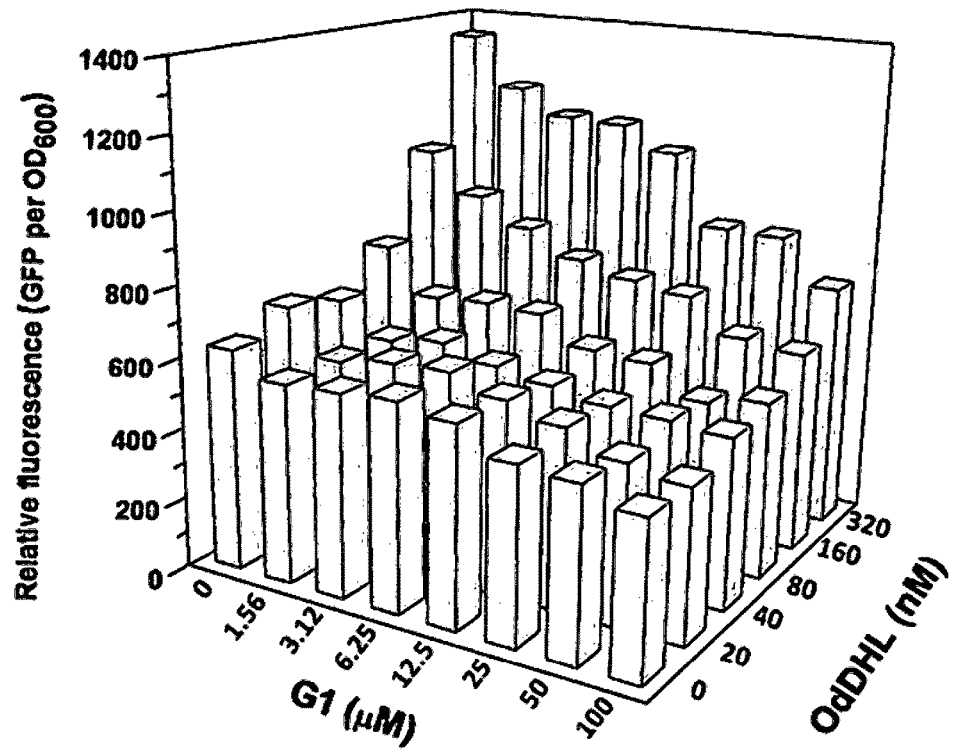
FIG. 7 shows the response of the *E. coli* lasB-gfp(ASV) strain to varying concentrations of 5-imino-4,6-dihydro-3H-1,2,3-triazolo[5,4-d]pyrimidin-7-one (G1) and OdDHL. Relative fluorescence is normalized through dividing GFP values by OD$_{600}$ values.

Of these 5 QSI candidates, only one compound, G1, was found to specifically inhibit LasR activity in the competition assay. The other four compounds did not show specific inhibition in the E. coli lasB-gfp (ASV) inhibition assay (FIG. 17(A)-(D)). FIG. 7 shows the relative fluorescence of the E. coli lasB-gfp (ASV) strain in response to varying concentrations of G1 and OdDHL. It can be seen that increasing levels of OdDHL increase lasB-gfp expression, while increasing levels of QSI decrease it. The highest amount of relative fluorescence was observed for the condition of no G1 and 320 nM OdDHL (value=1340.4) and the lowest amount of relative fluorescence for the condition of 100 µM G1 and no OdDHL (value=438.1). The relative fluorescence values for the condition of 320 nM OdDHL with 100 µM G1, and the condition without OdDHL or G1, are 711.5 and 627.6 respectively. In the presence of 320 nM OdDHL, 46.9% inhibition by 100 µM G1 was obtained (as compared to the control without G1), while in the absence of OdDHL, only 30.2% inhibition by 100 µM G1 was obtained (as compared to the control without G1).

The results also show that even in the presence of 320 nM OdDHL, 1.56 µM of G1 was sufficient in inhibiting OdDHL-LasR induction of gfp expression. If the OdDHL concentration were to be increased further, an out-competition of G1 by OdDHL will eventually be seen, where lower levels of G1 would be ineffective in inhibiting gfp expression and only higher levels of G1 would be able to inhibit gfp expression. The EC$_{50}$ of OdDHL for LasR activation has been previously determined to be 10 nM, therefore the range of OdDHL concentrations used for this assay is considered relatively high.

Figure 8:
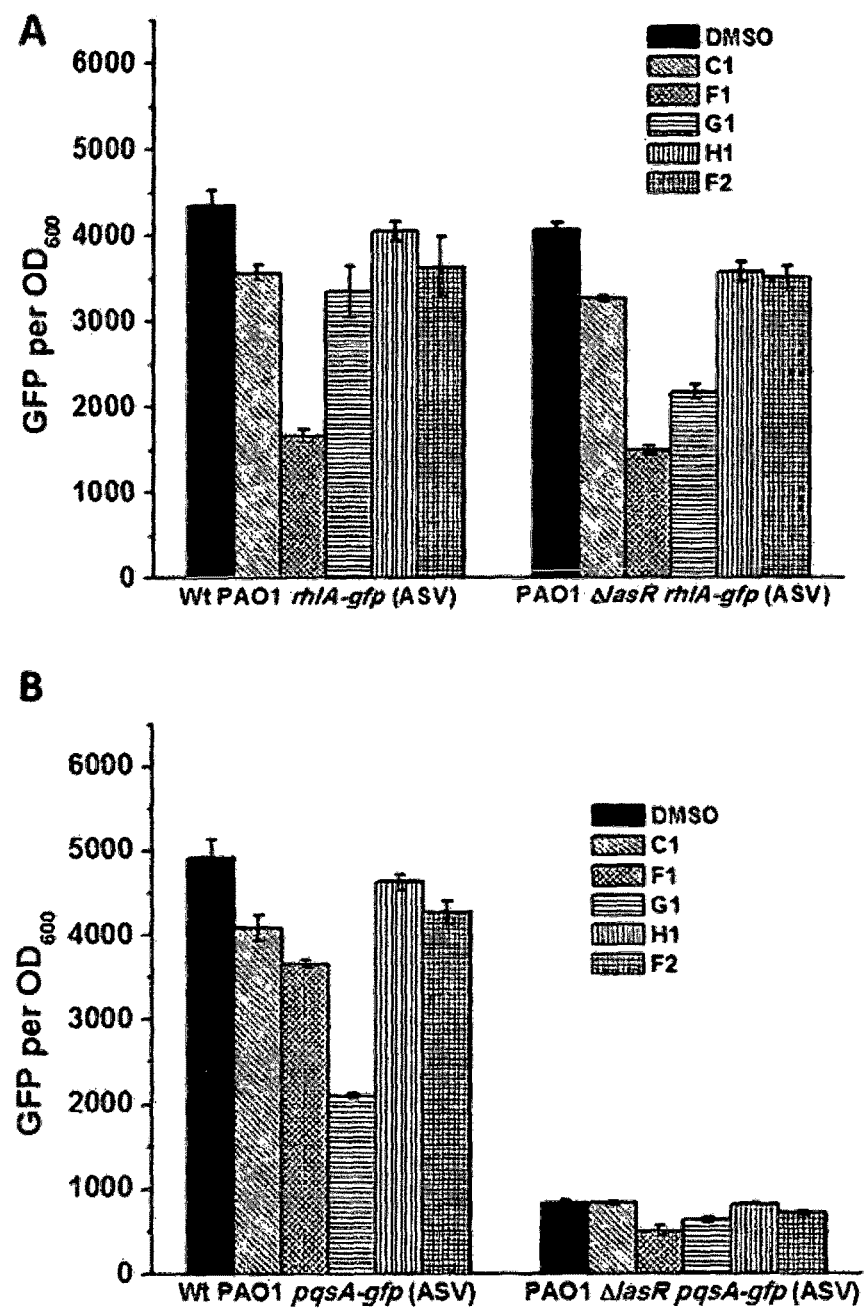
FIG. 8 shows the expression of: (A) rhlA-gfp(ASV); and (B) pqsA-gfp(ASV) in *P. aeruginosa* PAO1 wild-type and a lasR mutant when treated with 50 μM of each QSI. Results are the average relative fluorescence values (GFP readings divided by OD$_{600}$ values) from a single time point measurement corresponding to maximal induction of the reporters. Averages and standard deviation are from triplicate experiments.

Effect of QSIs on Rhl and Pqs Quorum-Sensing Systems. In order to address the problem of the specificity of present compounds, the five identified QSI compounds were tested to see if they had any effect on the rhl and pqs systems. The five QSIs were tested against a PAO1 wild-type and a PAO1 lasR mutant harboring either the rhlA-gfp (ASV) bioreporter or the pqsA-gfp (ASV) bioreporter. The rhlA system is dependent on the RhlR/I system. By doing so, we were able to determine if a QSI is able to inhibit the other two QS systems (i.e. rhl and pqs) in a lasR-dependent/independent manner (FIG. 8).

G1 was found to inhibit rhlA-gfp expression in the wild-type PAO1 strain (23.1% inhibition) and also in the lasR mutant (46.5% inhibition) (FIG. 8(A)). The P. aeruginosa rhl QS system uses a signal molecule BHL, which is structurally similar to the OdDHL of the las QS system, to regulate gene expression. Hence, it is likely that G1 as an inhibitor of LasR could also inhibit RhlR in the absence of LasR. Present results suggest that G1 has a higher binding specificity to LasR than RhlR.

G1 was observed to strongly inhibit pqsA-gfp expression in the wild-type PAO1 (57.5% inhibition) and lesser in the lasR mutant (24.4% inhibition) (FIG. 8(B)). Because the pqs QS system is positively regulated by the las system, inhibition of the las system by G1 would result in the down-regulation of the pqs expression. This shows that G1 inhibits the las QS system specifically, and inhibition of pqs is through a LasR-dependent mechanism.

Interestingly, F1 was able to inhibit both the rhl and pqs systems in a LasR-independent manner. F1 inhibited rhlA-gfp expression in the wild-type PAO1 by 61.7%, and in the lasR mutant showed an inhibition of 63.1% (FIG. 8(A)). F1 was also found to inhibit pqsA-gfp expression by 25.4% in the wild-type and 39.4% in the lasR mutant (FIG. 8(B)). Present results suggest that F1 has a higher binding specificity to RhlR than LasR.

Figure 9:
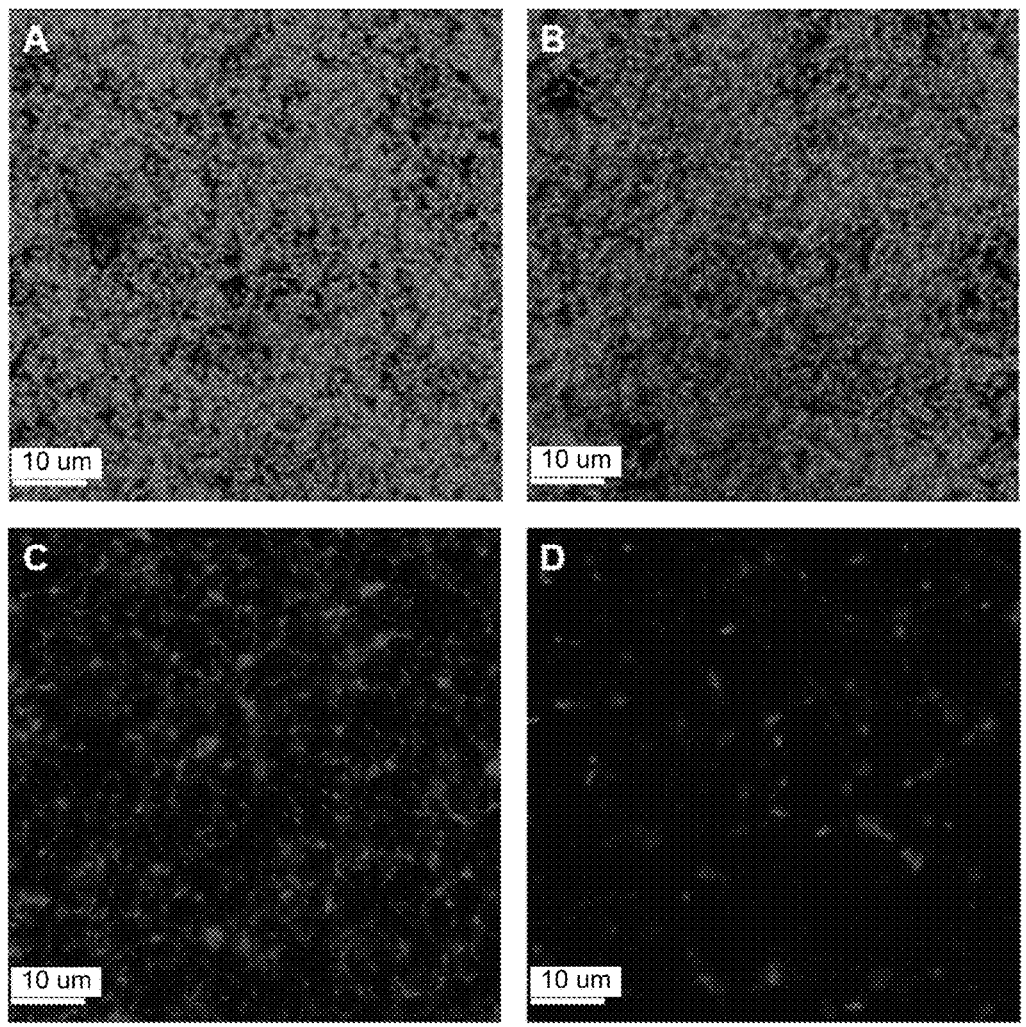
FIG. 9 shows biofilms of gfp-tagged PAO1 grown for 24 h either in ABTG medium (A and C) or in ABTG medium containing 10 μM G1 (B and D). These samples were stained with propidium iodide (PI). Images visualizing cells (green) and extracellular DNA (appearing red) were acquired by CLSM.

Effect of G1 on the extracellular DNA release in P. aeruginosa biofilms. The pqs QS system regulates release of extracellular DNA (eDNA), which is an important structure component for P. aeruginosa biofilms. Using a slide bio film assay, G1 was tested for its ability to reduce eDNA release in P. aeruginosa biofilms. Propidium iodide (PI) staining was used to stain and visualize eDNA. PI can stain both eDNA and dead cells, however, eDNA appears as string-like structures rather than circular structures indicative of dead cells. A large amount of eDNA was observed in the substratum of P. aeruginosa PAO1 biofilms cultivated in ABTG medium (FIG. 9(A), 9(C)) while less eDNA was observed in PAO1 biofilms cultivated in ABTG medium containing 25 µM G1 (FIG. 9(B), 9(D)). This indicates that G1 was able to reduce eDNA release in P. aeruginosa.

iTRAQ-Based Quantitative Proteomic Analysis. In order to study the proteins whose expression was down-regulated in P. aeruginosa PAO1 as a result of G1 addition, iTRAQ was used as the labeling strategy for comparative quantitative proteomic analysis (performed with a False Discovery Rate below 1%). The following cut-offs were used for protein identification: Unused Protein Score of at least 2 (i.e. 99% confidence of identification) and having more than 1 peptide identified. Using these cut-offs, 2258 proteins were identified. Using a p-value (115:114) cut-off of 0.05, 46 proteins were found to be significantly affected by G1; the abundance of 19 proteins was upregulated, while the abundance of 27 proteins was down-regulated. In present study, upregulation was defined as an abundance (115:114 score) of at least 1.5, and downregulation defined as an abundance value (115:114 score) below 0.66. FIG. 13 shows the 27 proteins whose abundance was significantly decreased in the G1-treated P. aeruginosa PAO1 strain versus the control PAO1 strain without G1 addition. Of these 27 proteins, ten had been previously found to be QS-regulated: protease IV, chitinase, hypothetical protein PA0572, pyoverdine synthetase D, pyoverdine chromophore synthetase PvdL, AmbE, probable non-ribosomal peptide synthetase, chitin-binding protein CbpD precursor, conserved hypothetical protein PA0588 and cystathionine beta-synthase.

Nouwens et al. (2003 *Proteome analysis of extracellular proteins regulated by the las and rhl quorum sensing systems in Pseudomonas aeruginosa* PAO1. Microbiology 149: 1311-1322) performed a proteomic analysis of the extracellular proteins regulated by the las and rhl systems in *P. aeruginosa*. In that study, it was found that the expression of protease IV (PA4175) to be significantly down-regulated in a las mutant. However, the amount of down-regulation was not quantified. In present study, the abundance of protease IV (PA4175) was found to be 0.29 (fold change −1.79). Protease IV is an extracellular protease that causes tissue damage in *P. aeruginosa* infections. Hence, reducing the expression of this virulence factor may attenuate *P. aeruginosa* virulence. Garlic extract and 4-nitropyridine-N-oxide (4-NPO) were also found to reduce the expression of protease IV by −6.9 and −20.7 fold, respectively.

Protease IV, also known as PrpL, is regulated by PvdS, which is an alternative sigma factor that regulates genes involved in siderophore biosynthesis genes. pvdS gene expression is regulated by the iron-sensing Fur repressor protein, such that pyoverdine is produced only in iron-limiting conditions. Therefore, G1 may act through the interaction with the Fur protein to inhibit PvdS-regulated induction of pyoverdine synthesis genes.

In support of this idea, the abundance of two pyoverdine synthetases were found to be significantly reduced: pyoverdine synthetase D (pvdD; PA2399) by −0.89 fold and pyoverdine chromophore synthetase (pvdL; PA2424) by −0.73 fold. Pyoverdine is a siderophore that is required for iron acquisition, and siderophore-mediated signalling regulates the expression of several virulence factors. In a recent study by Taguchi et al. (2009 *The siderophore pyoverdine of Pseudomonas syringae pv. tabaci 6605 is an intrinsic virulence factor in host tobacco infection.* J Bacteriol 192:117-126), a pvdL mutant of the *Pseudomonas syringae* pv. tabaci 6605 strain exhibited reduced virulence on host tobacco plants. The production of exopolysaccharide (EPS) and AHL was reduced, and this pvdL mutant was less tolerant to antibiotic (chloramphenicol and spectinomycin) treatment. Further testing would be required to find out if G1 could affect the resistance of *P. aeruginosa* to antibiotics.

In the proteomics result for G1, elastase (lasB; PA3724), a virulence factor that is known to be induced by the las system, was not identified as down-regulated. In another study, garlic extract and 4-NPO reduced the expression of elastase by −6.8 and −22.6 fold, respectively. Other QSIs such as patulin and penicillic acid reduced elastase expression by −7 and −12 fold, respectively, and in the *P. aeruginosa* PAO1 lasR mutant, elastase expression was decreased −13 fold. Hence, it was rather surprising not to find elastase on the list of down-regulated proteins. Thus, we decided to use an enzymatic assay to test if elastase production was significantly reduced with the addition of G1.

Figure 10:
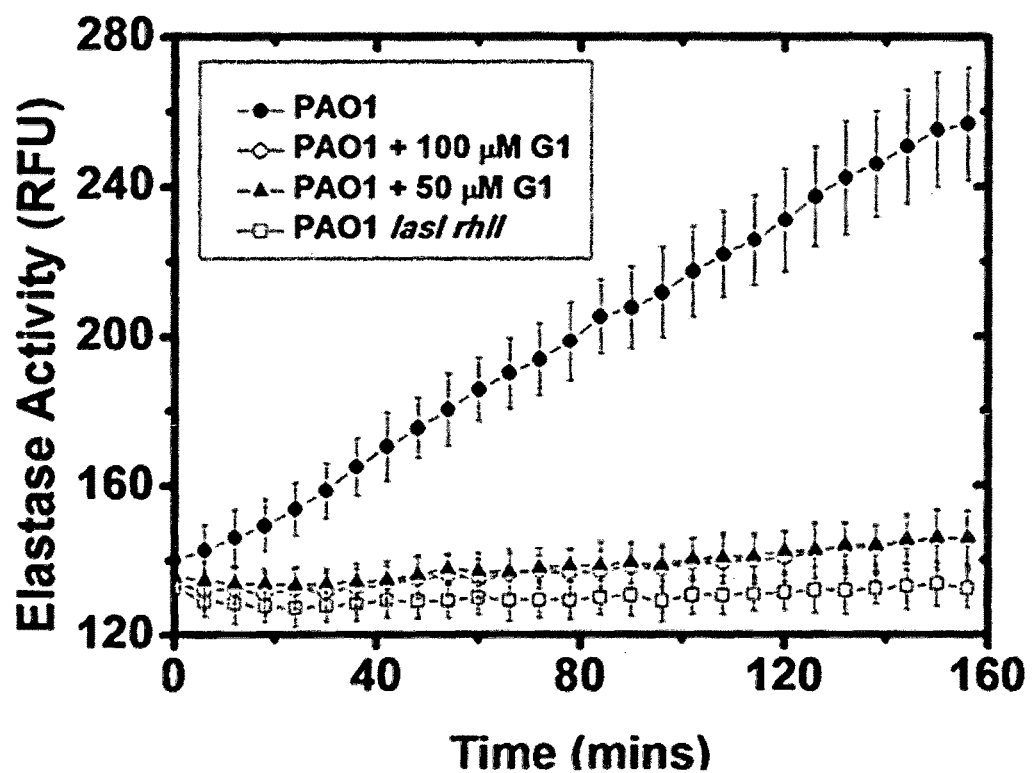
FIG. 10 shows the effect of G1 on the elastase activity of *P. aeruginosa* cultures. Elastase activity of *P. aeruginosa* culture supernatants was measured by using the EnzChek-Elastase Assay Kit (Invitrogen). Fluorescence was recorded every 6 min for 180 min by using a Tecan Infinite 200 Pro plate reader (excitation at 490 nm, emission at 520 nm). The *P. aeruginosa* PAO1 lasI rhlI strain served as a negative control.
Figure 17:
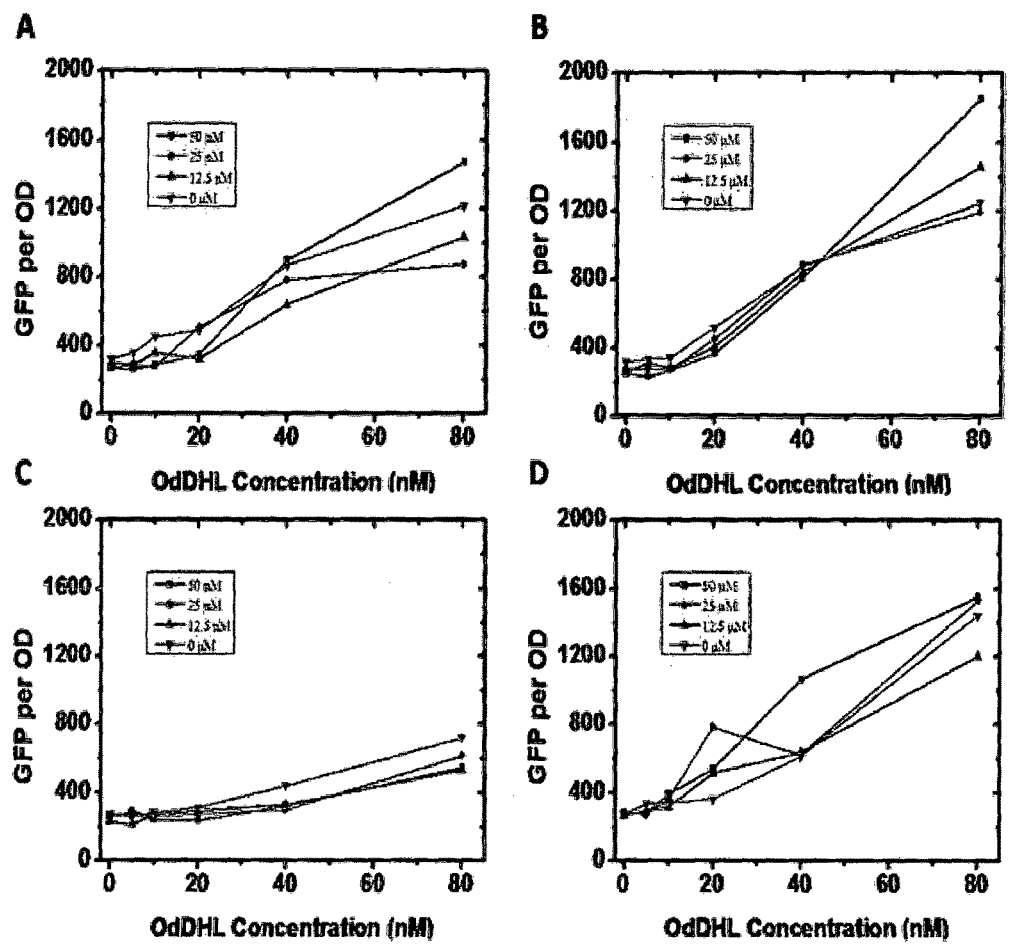
FIG. 17 shows competition assay results of the following 4 QSIs when incubated with *E. coli* lasB-gfp(ASV) strain and increasing concentrations of OdDHL: (A) 6-hydro-3H-1,2,3-triazolo[5,4-d]pyrimidin-7-one (C1); (B) 2-amino-3-(3-fluorophenyl)propanoic acid (F1); (C) indole-3-carboxylic acid (F2); and (D) 2-amino-3-hydroxy-3-phenylpropanoic acid (H1). The legend refers to the concentrations of the respective QSI used.

Effect of G1 on the Production of Elastase by *P. aeruginosa*. The metalloprotease elastase B is a las QS system regulated virulence factor produced and excreted by *P. aeruginosa*. QSIs that inhibit the las QS system should be able to inhibit the production of elastase B. A standard enzymatic assay was used to test whether G1 could inhibit the elastase activity of *P. aeruginosa* cultures. The result showed that addition of G1 to *P. aeruginosa* PAO1 cultures at 50 and 100 μM could almost abolish elastase production within 2 h cultivation period (FIG. 10), matching the levels of a *P. aeruginosa* PAO1 lasI rhlI mutant. This *P. aeruginosa* PAO1 lasI rhlI mutant is deficient in quorum-sensing and used as a negative control. The amount of elastase produced by *P. aeruginosa* upon exposure to G1 was similar to this negative control, which indicates that G1 was efficient in inhibiting elastase production.

Discussion. In a previous study by Yang et al. (2009 *Computer-aided identification of recognized drugs, as Pseudomonas aeruginosa quorum-sensing inhibitors.* Antimicrob Agents Chemother 53:2432-2443), 147 compounds were screened based on structural similarity to the ligand OdDHL. Six top-scoring hits were identified and tested for QSI activity. Of these identified compounds, three were found to have dose-dependent inhibition of QS-related gene expression and associated phenotypes. In the present study, DG-AMMOS was used to enhance in silico QSI discovery. One advantage of using DG-AMMOS, rather than relying on structural similarity to the ligand of interest, is the avoidance of rational bias in the screening process, therefore allowing the detection of lead compounds that may not be able to be identified rationally. Hence, it is possible that DG-AMMOS can be extended to the conversion of larger compound libraries (e.g. 10,000 compound libraries, combinatorial chemistry libraries) and allows the discovery of new compounds that may have little structural similarity to QSIs or AHLs, yet possess QSI properties.

SB-VS has been used extensively in the pharmaceutical industry. Famous examples include Relenza, an anti-influenza drug that targets sialidase and Viracept, a human immunodeficiency virus protease inhibitor. In recent years, SB-VS approaches have also been used in the search for novel QSIs, and here are a few recent examples: (1) discovery of hamamelitannin, a natural compound from *Hamamelis virginiana* that inhibits QS in drug-resistant *Staphylococcus aureus* and *S. epidermidis*; (2) identification of novel AI-2 QS inhibitors of *Vibrio harveyi* by SB-VS with the crystal structure of LuxP; (3) discovery of a compound from *Melia dubia* bark extract which could inhibit the QS regulator SdiA present in uropathogenic *E. coli* (UPEC); (4) discovery of five QSIs from a SB-VS of 1,920 natural compounds against the LasR and RhlR receptor proteins; (5) discovery of 5 inducers and 3 inhibitors of LasR through a SB-VS of 800,000+ compounds from the Chembridge library through a pharmacophore-based approach for compounds similar to OdDHL.

One major limitation of SB-VS is the problem of false-positives and false-negatives predicted by the docking software. However, with the development of newer and better algorithms, the problem of false hits may be minimized. Also, the aim may not be to eliminate false-positives entirely, but to reduce it to a tolerable level, reason being that false-positives may lead to the discovery of novel molecular interactions. As such, the cutoff of a −60 Rerank Score that was used in present study for identifying potential QSI candidates might have been too stringent, and a higher value (i.e. less negative) could have been used instead so as to increase the number of potential hits. However, using a less stringent cut-off would increase the number of false-positives, and this trade-off between the number of potential leads and the number of false-positives must be considered for all SB-VS studies.

On the whole, SB-VS methods provide a faster and cheaper alternative to HTS approaches for several reasons. Firstly, if the search strategy in SB-VS is restricted to commercially available compound libraries, the lead compounds identified through SB-VS can be purchased easily and one does not need to undertake a costly chemical synthesis process. Secondly, SB-VS can be used to dock known drugs or natural plant derivatives, which would be likely to have lower toxicity than compounds synthesized through combinatorial chemistry. Thus, compounds identified through screening of known drugs/natural product libraries can avoid failure in the in vitro and in vivo testing stages due to toxicity. Lastly, SB-VS is able to first narrow down the list of compounds to be tested before proceeding with actual in vitro tests for efficacy, and this would greatly reduce costs as compared to conventional HTS methods where all compounds have to be tested.

In present study, it is shown that structure-based virtual screening is a viable and effective means for the discovery of novel QS inhibitors. From a library of 3,040 natural compounds, 22 compounds met selection criteria and were tested for biological activity. Five of these compounds were found to have dose-dependent inhibition of the las QS system. However, only G1 was shown to have dose-dependent inhibition of lasB-gfp in both the *P. aeruginosa* and the *E. coli* strains, indicating its specificity for the LasR protein. Among the five QSI candidates, G1 had the lowest $IC_{50}$ of 0.64 µM.

G1 was also able to delay the induction of the rhl QS system (data not shown). G1 showed some inhibition of the rhl QS system. Perhaps it either has very weak binding affinity or allosteric effects. This may be due to the presence of the homoserine lactone ring present in both the LasR ligand, OdDHL, and the RhlR ligand, BHL. Studies have shown that the lactone ring is important for interaction with the LasR binding pocket. Presumably, a RhlR structure would be very useful to help understand the differences in the binding pockets and hence the binding of compounds like G1. However, the crystal structure of RhlR is unavailable, so homology modeling may be used to generate a putative structure for docking studies.

Besides the rhl system, G1 was also found to repress the PQS system. Previous studies have shown that the las QS system positively regulates the pqs QS system and the results of present study suggest that G1 represses expression of the PQS system through inhibition of the las QS system. The pqs QS system regulates release of eDNA, which is an important structural component for *P. aeruginosa* biofilms. As such, it was found that G1 was able to reduce the amount of eDNA being released by *P. aeruginosa*.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A method for the treatment of a bacteria-related disease or disorder caused by *Pseudomonas aeruginosa* in a subject having the bacteria-related disease or disorder, wherein the method comprises:
    administering a therapeutically effective amount of a compound selected from the group consisting of:

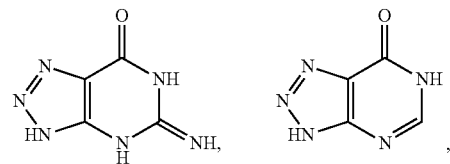 [SMILES: N=c1[nH]c(=O)c2nn[nH]c2[nH]1 ; O=c1[nH]cnc2[nH]nnc12]

and combinations thereof;
    wherein the subject is a mammal; and
    wherein the disease or disorder is selected from endocarditis, respiratory and pulmonary infections, bacteremia, central nervous system infections, ear infections, eye infections, bone and joint infections, urinary tract infections, gastrointestinal infections, skin infections, soft tissue infections, pyoderma, dermatitis and combinations thereof.

2. The method of claim 1, wherein the compound is

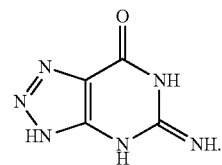

* * * * *